(12) United States Patent
Kanegasaki et al.

(10) Patent No.: US 7,259,008 B2
(45) Date of Patent: Aug. 21, 2007

(54) MICROSAMPLE TREATMENT APPARATUS

(75) Inventors: Shiro Kanegasaki, Kawasaki (JP); Yuji Kikuchi, Ryugasaki (JP)

(73) Assignee: Effector Cell Institute, Tokyo (JP)

( * ) Notice: Subject to any disclaimer, the term of this patent is extended or adjusted under 35 U.S.C. 154(b) by 481 days.

(21) Appl. No.: 10/181,707

(22) PCT Filed: Dec. 6, 2001

(86) PCT No.: PCT/JP01/10684

§ 371 (c)(1),
(2), (4) Date: Jul. 22, 2002

(87) PCT Pub. No.: WO02/46356

PCT Pub. Date: Jun. 13, 2002

(65) Prior Publication Data

US 2003/0003570 A1    Jan. 2, 2003

(30) Foreign Application Priority Data

| Dec. 7, 2000 | (JP) | 2000-372467 |
| Jul. 10, 2001 | (JP) | 2001-209743 |
| Nov. 8, 2001 | (JP) | 2001-343713 |

(51) Int. Cl.
*C12M 1/34* (2006.01)

(52) U.S. Cl. ............... 435/288.5; 435/297.1; 435/297.5; 435/288.7; 422/101; 422/102

(58) Field of Classification Search ............ 435/286.4, 435/288.5, 288.7, 297.5, 288.4, 297.1; 422/101, 422/102
See application file for complete search history.

(56) References Cited

U.S. PATENT DOCUMENTS

| 3,888,770 A | 6/1975 | Avital et al. |
| 3,929,583 A | 12/1975 | Sharpe et al. |
| 4,317,726 A | 3/1982 | Shepel |
| 4,493,815 A | 1/1985 | Fernwood et al. |
| 4,514,495 A | 4/1985 | Schalkowsky et al. |
| 4,714,674 A | 12/1987 | Palladino |
| 4,729,949 A | 3/1988 | Weinreb et al. |
| 4,895,805 A | 1/1990 | Sato et al. |

(Continued)

FOREIGN PATENT DOCUMENTS

EP    0 368 241 A2    5/1990

(Continued)

OTHER PUBLICATIONS

Cutler, J. et al., Proc. Soc. Exp. Biol. Med., 147: 471-474 (1974).

(Continued)

*Primary Examiner*—William H. Beisner
(74) *Attorney, Agent, or Firm*—Birch, Stewart, Kolasch & Birch, LLP

(57) ABSTRACT

A microsample treatment apparatus and an apparatus for detecting chemotaxis of cells and separating chemotactic cells includes a number of wells that are connected to each other via a part having resistance to fluids. The wells are each provided with tubes for injecting/sucking a sample and, if necessary, tubes for relieving pressure changes at the injection/suction. The tubes have a space in common at the top ends thereof in which a liquid can be held.

12 Claims, 29 Drawing Sheets

U.S. PATENT DOCUMENTS

| | | | |
|---|---|---|---|
| 4,912,057 | A | 3/1990 | Guirguis et al. |
| 5,284,753 | A | 2/1994 | Goodwin, Jr. |
| 5,302,515 | A | 4/1994 | Goodwin, Jr. |
| 6,395,505 | B2 | 5/2002 | Goodwin, Jr. |
| 6,451,608 | B1 * | 9/2002 | Kikuchi .................. 436/63 |
| 2002/0086280 | A1 | 7/2002 | Lynes et al. |

FOREIGN PATENT DOCUMENTS

| | | |
|---|---|---|
| EP | 368241 A2 | 5/1990 |
| JP | 3-257366 A | 11/1991 |
| JP | 257366/1991 | 11/1991 |
| JP | 8-23967 A | 1/1996 |
| JP | 23967/1996 | 1/1996 |
| JP | 11-165062 A | 6/1999 |
| JP | 165062/1999 | 6/1999 |
| WO | 94/16098 A1 | 7/1994 |
| WO | WO94/16098 A1 | 7/1994 |
| WO | 96/03206 A1 | 2/1996 |
| WO | WO96/03206 A1 | 8/1996 |
| WO | WO 00/07007 A1 | 10/2000 |
| WO | WO 01/32827 A1 | 10/2001 |

OTHER PUBLICATIONS

John, T. J. et al., Life Science, 18:177-182 (1976).
Harvath, L. et al., Journal of Immunological Methods, 37:39-45 (1980).
Zigmond, S. H. et al., Annual Review of Medicine, 37:149-155 (1986).
Falk, W. et al., Journal of Immunological Methods, 33:239-247 (1980).
Gatewood, B. et al., Journal of Immunology, 147:243-246 (1991).
Falk, W. et al., Infection and Immunity; 36:450-454 (1982).
Harvath, L. et al., Infection and Immunity, 36:443-449 (1982).
Richards, K. K. et al., Immunological Communications, 13:49-62 (1984).
Nelson, R. D. et al., J. Immunol., 115:1650-1656 (1975).
Repo, H., Scand. J. Immunol., 6:203-209 (1977).
Junger, W. G. et al., J. Immun. Methods, 160:73-79 (1993).
Kikuchi, Y. et al., Microvascular Research, 44:226-240 (1992).
Kikuchi, Y. et al., SPIE 2978:165-171 (1997).
Kikuchi, Y. et al., Journal of the Japan Society for Precision Engineering, 62:1553-1556 (1996).
Kikuchi, Y. et al., Chemical Engineering, 62:136-138 (1998).
Kikuchy, Y. et al., Biophysics 37:254-258 (1997).
Zigmond, S. H., J. Cell Biology 75:606-616 (1977).
Allen, W. E. et al., J. Cell Biology, 141:1147-1157 (1998).
Zicha, D. et al., J. Cell Science 99:769-775 (1991).
Neuro Probe, Inc. "Neuro Probe Zigmond Chamber", no date provided.
Weber Scientific, Inc. "Dunn Chemotaxis Chamber", no date provided.
Boyden, Department of Experimental Pathology, John Curtin School of Medical Research, Australian National University, Canberra, pp. 453-466 (1961).
Francis et al., Proc. Natl. Acad. Sci. USA, vol. 94, pp. 12258-12262 (Nov. 1997).
Kikuchi, Microvascular Research, vol. 50, pp. 288-300 (1995).
Kobayashi et al., J. Biochem, vol. 117, pp. 758-765 (1995).
Lehninger, Biochemistry, Second Edition, *The Molecular Basis of Cell Structure and Function*, pp. 173-181 (1978).
Mazumder et al., Journal of Crystal Growth, vol. 224, pp. 165-174 (2001).
Junger et al., Journal of Immunological Methods, vol. 160, No. 1, pp. 73-79 (1993).

* cited by examiner (1)

(2)

(1)

(2)

(1)

(2)

MICROSAMPLE TREATMENT APPARATUS

This application is the national phase under 35 U.S.C. § 371 of PCT International Application No. PCT/JP01/10684 which has an International filing date of Dec. 6, 2001, which designated the United States of America.

TECHNICAL FIELD

This invention relates to an apparatus for treating liquid samples in microquantities. More particularly, it relates to a microsample treatment apparatus having a structure whereby, in the step of injecting a liquid sample into a microwell for holding a sample to be reacted, analyzed, detected, etc., the overflow of the sample or the migration thereof into another well connected thereto can be prevented and the position of the sample in the microwell can be adjusted.

The present invention further relates to an apparatus for judging whether or not cells can migrate in a definite direction by their own actions, observing the state of cells migrating in a definite direction by their own actions, or counting cells having migrated in a definite direction by their own actions (i.e., an apparatus for detecting chemotaxis of cells). Furthermore, the present invention relates to an apparatus for separating cells based on the selective migration of cells by their own actions. More particularly speaking, it relates to an apparatus for detecting chemotaxis of cells or separating chemotactic cells having a structure wherein, in the step of injecting a liquid sample into a microwell for holding a cell suspension or a specimen/sample to be detected, separated, etc., the overflow of the sample or the migration thereof into another well connected thereto can be prevented and the position of the sample in the microwell can be adjusted.

BACKGROUND ART

With the recent development and progress in nanotechnology, it has been apractice to handle cells, proteins, genes and so on at a level of several individuals. As a result, it becomes necessary to inject and treat microsamples into containers (wells) for reaction, analysis or detection. To carry out a series of reactions, analyses, detections, etc. on microchips, use is sometimes made of a structure wherein a plural number of wells are connected to each other each via a pipe, a groove or a channel. In such a case, attention should be taken to prevent the migration of a sample into the adjacent well due to the injection pressure, which brings about some difficulties not only in manual operations but also in operations with the use of an automatic injection device. It is also desired to adjust the position of a sample injected into a microwell or to transfer the sample into the next well while adjusting the position.

It is an object of the present invention to provide a structure to be used in the above-described apparatus whereby, in the step of injecting a microsample into a well, the migration of the sample into another well or overflow from the well can be certainly prevented. It is another object of the present invention to provide a structure wherein the position of an injected sample in a well can be adjusted or the sample can be transferred into the next well under controlling. It is still another object of the present invention to provide a microsample treatment apparatus wherein a sample can be injected and transferred under automated control.

It is still another object of the present invention to provide an apparatus for detecting chemotaxis of cells or separating chemotactic cells with the application of the structure having the functions as described above.

DISCLOSURE OF THE INVENTION

The present invention relates to a microsample treatment apparatus having a structure wherein a plural number of wells are connected to each other via a part having resistance to fluids and the wells are each provided with tubes for injecting/sucking a sample and, if necessary, tubes for relieving pressure changes at the injection/suction, characterized in that these tubes have a space in common at the top ends thereof in which a liquid can be held. The part having resistance to fluids may be selected from among one or more thin pipes, narrow gaps, thin grooves, filters, resin-filled columns and other structures through which a fluid can be passed but which have resistance to fluids.

The present invention further relates to a microsample treatment apparatus wherein the top end of a tube formed in a well is located upper than the top ends of the tubes formed in one or more wells opposite thereto across the part having resistance to fluids. The microsample treatment apparatus according to the present invention may have, in one or both of wells connected to each other via a channel, a wall formed orthogonal to the channel to thereby restrict the amount of a liquid in the vicinity of the channel.

The present invention relates to a microsample treatment apparatus which comprises a unit part having a single unit selected from the microsample treatment apparatuses as described above, an integration unit having a plural number of units of the same or different types or a plural number of integration units, a pipette or pipettes for controlling the liquid level in the unit part, and a system for controlling the operation of the liquid level control pipette(s). Moreover, the present invention relates to an automated microsample treatment apparatus characterized in that the liquid level control pipette(s) are controlled so as to suck a definite amount of a liquid contained in the space held in common by a plural number of tubes at the top ends thereof in each of the units in the unit part, thereby adjusting the position of the sample in well(s) or transferring the sample into the respective next well(s) followed by, if necessary, supplying the liquid in a compensatory amount to return the liquid face to the original level. If necessary, the microsample treatment apparatus may be provided with a sample reservoir, a specimen reservoir, pipette(s) washing part and sample supply pipette(s) and specimen supply pipette(s) which are movable over these parts and further have a system for controlling the operations of these pipettes. The materials of the pipettes are not restricted to glass but can be appropriately selected from among metals, plastics and the like.

The present invention involves in its scope an apparatus for detecting chemotaxis of cells or separating chemotactic cells characterized in that a plural number of wells are connected to each other via a part having resistance to fluids, the wells are each provided with tubes for injecting/sucking a sample and, if necessary, tubes for relieving pressure changes at the injection/suction, these tubes have a space in common at the top ends thereof in which a liquid can be held, and the wells are closely adhered to a glass substrate in the side opposite to the tube side.

The present invention further relates to an apparatus for detecting chemotaxis of cells or separating chemotactic cells as described above characterized in that the top end of a tube formed in a well for holding cells is located upper than the top ends of the tubes formed in one or more wells opposite thereto across the channel having resistance to fluids.

In the present invention, it is preferable that the channel having resistance to fluids is a bank and a narrow gap is formed between the bank and the glass substrate. In this case, a terrace may be formed in the upper part of the bank in the channel to form a gap between the terrace and the glass substrate. Alternatively, barriers constituting one or more grooves having a width fit for the diameter or deformability of cells may be formed in the upper part of the bank and, if necessary, a terrace may be further formed together with the bank to form a gap fit for the diameter or deformability of cells between the terrace and the glass substrate too. A plural number of grooves in the direction toward the opposite well in the channel may be connected to each other via one or more grooves orthogonal thereto. It is also possible that the width of a plural number of grooves in the direction toward the opposite well in the channel is changed stepwise each time the grooves intersect one or more grooves orthogonal thereto. Furthermore, a plural number of grooves in the direction toward the opposite well in the channel may be formed by mutually shifting the positions thereof each time the grooves intersect one or more grooves orthogonal thereto. Moreover, arrays of the barriers constituting the grooves may be formed at two positions in both sides of the terrace formed at the center of the bank. It is also possible that multistage terraces are formed on the bank in the channel so as to form gaps with different depths between the terrace and the glass substrate. In one or both of wells connected to each other via a channel, moreover, a wall may be formed orthogonal to the channel to thereby restrict the amount of a liquid in the vicinity of the channel.

The present invention relates to an automated apparatus for detecting chemotaxis of cells or separating chemotactic cells comprising a unit part having a single unit selected from the apparatuses for detecting chemotaxis of cells or separating chemotactic cells as described above, an integration unit having a plural number of units of the same or different types or a plural number of integration units, a cell reservoir, a specimen reservoir and liquid level control pipette(s), cell supply pipette(s) and specimen supply pipette(s) which are movable over these parts, and further having a detection part for detecting cell migration in the unit part and, if necessary, recording the detection data which is integrated with the unit part or formed so as to correspond to a plural number of unit parts, and further having a system for controlling the movements of the liquid level control pipette(s), the cell supply pipette(s) and the specimen supply pipette(s) and, if necessary, a system for moving the unit part to the detection part and the next unit part to the pipette flow line. If necessary, this apparatus may further have a pipette washing part.

The present invention further relates to an automated apparatus for detecting chemotaxis of cells or separating chemotactic cells characterized in that the operations of the respective pipettes are controlled as follows: after optionally stirring, a definite amount a cell suspension is sucked by the cell supply pipette(s) and supplied into the unit part; then a definite amount of a liquid, which is contained in the space held by the top ends of a plural number of tubes in common in each unit, is sucked by the liquid level control pipette(s) to thereby adjust the position of the cells in the wells; the liquid in the compensatory amount is supplied from the liquid level control pipette(s) into the space to thereby return the liquid face to the original level; then a definite amount of a specimen is sucked from the specimen reservoir by the specimen supply pipette(s) and supplied into the unit part; then the pipettes move toward the pipette washing part in which they are washed by repeatedly sucking and discharging the washing liquor.

DESCRIPTION OF THE REFERENCE NUMERALS AND SIGNS

Figure 1:
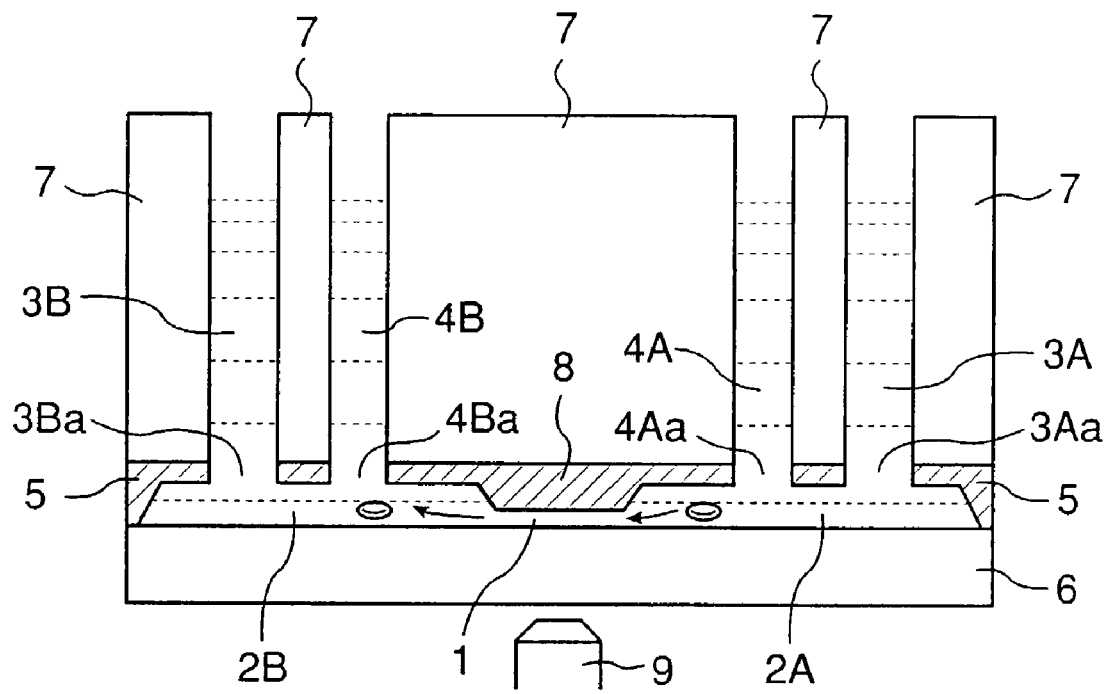
FIG. 1 is a model view which shows an example of an apparatus for detecting chemotaxis of cells or separating chemotactic cells previously proposed by the present inventors.

1: channel.
2: well. Appendixes A, B, $B_{1-n}$, and C are provided to differentiate the wells.
3: tube for injecting/collecting samples. Appendixes A, B, $B_{1-n}$, and C are provided to differentiate the wells. Appendix a represents a penetrating hole corresponding to a tube 3 of a substrate 5. Appendix b represents the top end of the tube 3.
4: tube for avoiding increase/decrease in pressure at injecting/collecting samples. Appendixes A, B, $B_{1-n}$, and C are provided to differentiate the wells. Appendix a represents a penetrating hole corresponding to a tube 4 of a substrate 5. Appendix b represents the top end of the tube 4.
5: substrate.
5': packing.
6: glass substrate.
7: block having tube mounted thereto.
8: bank.
9: detector.
10: space held together by top ends of tubes.
11, $11_{-1\ to\ 4}$: terraces.
12: barrier in channel 1.
13: groove in the direction toward the opposite well across channel.
14: groove formed orthogonally to groove 13.
15: magnet.
16: column located between wells.
17: cover cap.
18: O-ring.
19: guide pin receiver hole.
20: guide pin.
21: intermediate base.
22: bottom base.
23: bottom substrate.
24: wall formed along channel.
25: cell reservoir.
26: cell injection part.
27: liquid injection part.
28: specimen reservoir.
29: pipette tip inlet port.
30: pipette washing part.
31: multichannel syringe.
32: actuator.
33: needle of automatic pipette.
34: tip of manual pipette.
←: level of liquid filling up apparatus.
←I: level of liquid making the top end of upper tube submerged.
←II: level of liquid making the top end of upper tube visible above the liquid face.
X-X': flow line of specimen supply pipette.
Y-Y': flow line of cell supply pipette.
Z-Z': flow line of liquid level control pipette.

BEST MODE FOR CARRYING OUT THE INVENTION

The microsample treatment apparatus according to the present invention provided with wells into which a sample such as a liquid or a suspension is injected is an apparatus for handling organic or inorganic chemicals, polymers such as proteins, genes, cells and so on in the state of solutions or suspensions. Although the structure of the present invention is not specifically restricted in the amount of samples to be treated, it is expected that high technical merits can be achieved thereby in case of using samples of the order of several milliliters to microliters.

The present invention is applied to case wherein a plural number of wells are connected to each other via a structure having resistance to fluids and the wells are each provided with tubes for injecting or sucking a sample and, if necessary, tubes for relieving pressure changes at the step of the injecting or sucking the sample. That is, such an apparatus has a plural number of tubes as a whole. In the present invention, these tubes have a space in common at the top ends thereof in which a liquid can be held. Owing to this structure, unexpected migration and overflow caused by a rapid change in pressure in the wells in the step of injecting or sucking a sample or unexpected migration of the sample caused by horizontal off balance of the apparatus can be effectively prevented.

By employing the structure wherein a plural number of tubes have a space in common at the top ends thereof in which a liquid can be held, the position of a sample can be adjusted in a microwell or the sample can be transferred into the next well under controlling, in case of handling samples the position of which should be adjusted in the well or which should be transferred into the next well. To further ensure the control and migration, the top end of a tube formed in the well for holding the sample is located upper than the top ends of tubes formed in other wells.

To enable the migration of a sample among a plural number of wells, the wells are usually connected to each other via, for example, thin pipes, narrow gaps, thin grooves, filers, resin-filled columns or channels. The present invention relates to an apparatus wherein a plural number of wells are connected to each other via such a structure having resistance to a fluid flow.

Now, illustration will be made on the application the present invention to an apparatus wherein a plural number of wells are connected to each other each via a channel, for example, an apparatus for detecting chemotaxis of cells or separating chemotactic cells. However, it is obvious from the description given above that the present invention is not restricted to apparatuses for detecting chemotaxis of cells or separating chemotactic cells but applicable to various apparatuses.

In the apparatus for detecting chemotaxis of cells or separating chemotactic cells, a cell suspension is put into one of the wells while a specimen solution is put into the other well. Then it is detected whether or not cells migrate toward the well holding the specimen solution, or cells which have migrated are selectively collected. In this apparatus, for example, the well holding the cell suspension is connected to the well holding the specimen solution via a channel. Thus, the state where the cells are passing through the channel is observed, or the cells which are passing or have passed through the channel are counted.

A channel which makes it possible to observe or detect the passage of individual cells has resistance to fluids. In an apparatus provided with such channels, it is sufficient to employ only a small amount of cells as a sample, which brings about a merit of being adequate for examining rare cells. In addition, there is another merit that quantitative analysis can be made. In this case, however, the whole apparatus is in a small size and thus samples should be handled in microquantities. As a result, there frequently arises unexpected migration of cells toward a well holding a specimen solution under the effect of an increase in pressure caused by the injection into the wells. In case the wells are not held horizontally after the injection, moreover, cells would migrate. These unexpected migrations of cells result in confusion in the judgment whether the specimen is a chemotactic factor or not. To accurately detect the migration of cells toward a well holding a specimen solution by their own actions, it is therefore required to prevent the migration of the cells at the point of injecting a sample or after the injection.

As one of countermeasures thereto, the present inventors have proposed a structure wherein each well has a tube for injecting a sample and an additional well connected thereto for relieving an increase in pressure at the injection (Japanese Patent Application No. 2001-226466). Now, this structure will be briefly described by reference to FIGS. 1 and 2.

Figure 2:
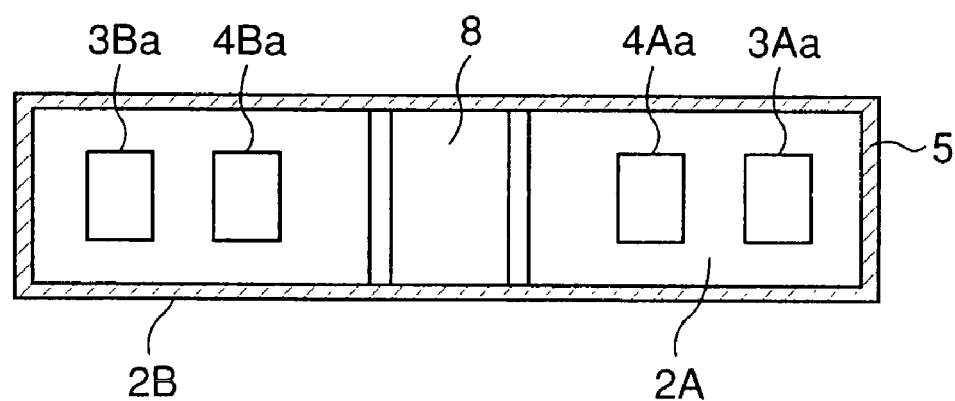
FIG. 2 is a bottom plan view of the apparatus of FIG. 1.

In the apparatus shown by FIG. 1, a cell suspension is injected into a well 2A through a tube 3A. A specimen solution is injected into a well 2B through a tube 3B. In case where this specimen contains a chemotactic factor, cells tend to migrate from the well 2A toward the well 2B and thus pass through the channel 1. In FIG. 1, a gap corresponding to the cell size is provided between a bank 8 formed on a substrate 5 and a transparent glass substrate 6. Alternatively, barriers constituting a plural number of thin grooves through which individual cells can pass may be formed. The state of the cells passing through the channel 1 can be observed by, for example, a microscope 9 through the glass substrate 6. FIG. 2 is a bottom plan view of the substrate 5.

In the apparatus shown by FIGS. 1 and 2, the tubes 3A and 4A and the tubes 3B and 4B are connected to each other in the respective wells. In this structure, pressure is dispersed through the tubes connected to each other. In the present invention, in contrast thereto, the top ends of all of the tubes formed in respective wells have a space in common in which a liquid can be held. Owing to this structure, the migration at the injection can be more surely relieved or the migration can be controlled (see FIGS. 3 and 4).

Figure 3:
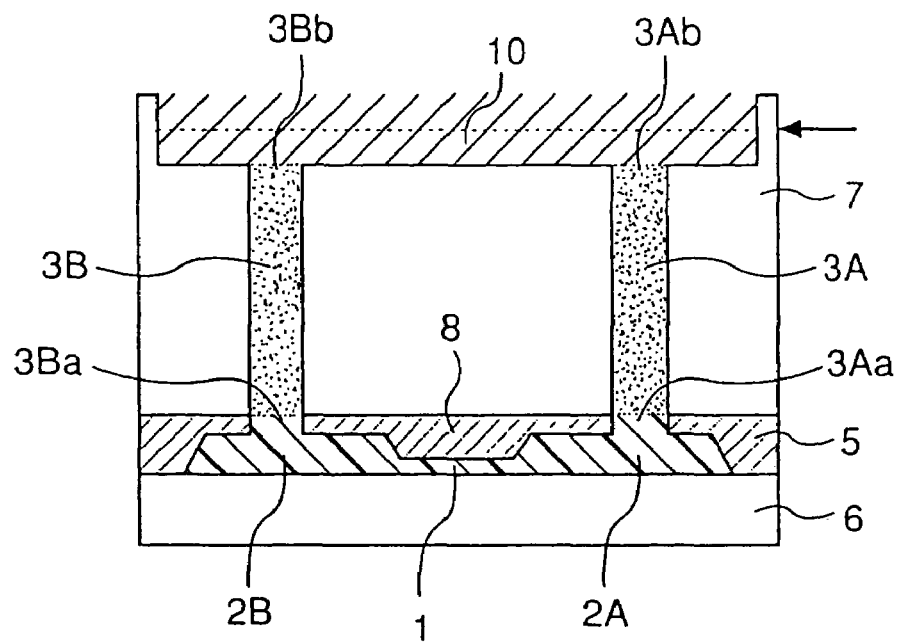
FIG. 3 is a model view which shows an example of the application of the structure according to the present invention to an apparatus for detecting chemotaxis of cells or separating chemotactic cells. The arrow shows the liquid level of a liquid filling up the apparatus.
Figure 4:
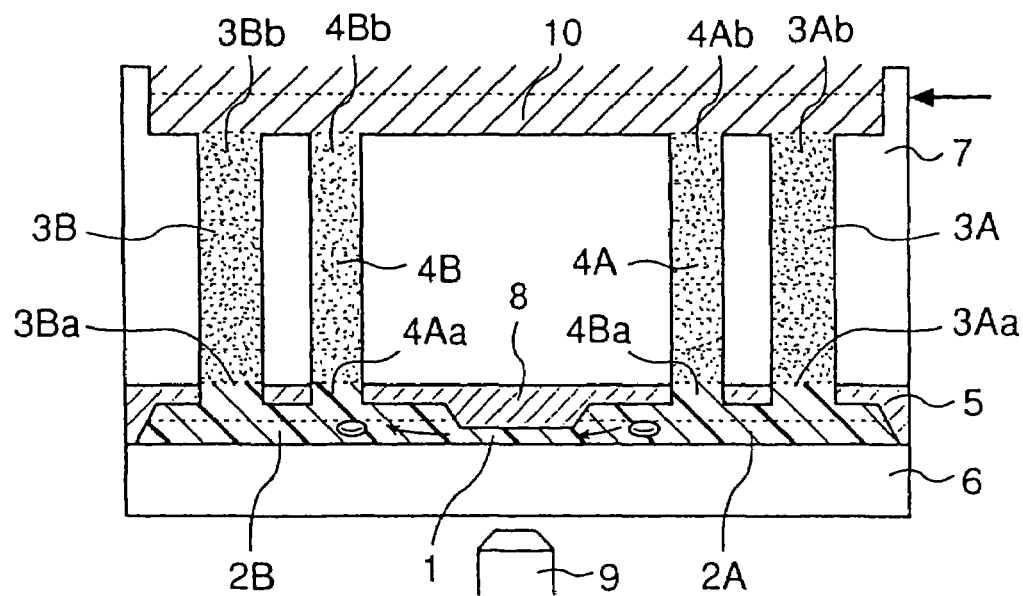
FIG. 4 is a model view showing another example of the application of the structure according to the present invention to an apparatus for detecting chemotaxis of cells or separating chemotactic cells which is provided with tubes 3 for injecting/collecting a sample into wells and tubes 4 for relieving decrease/increase in pressure at the step of injecting/collecting the sample. The arrow shows the liquid level of a liquid filling up the apparatus.

FIG. 3 shows an example of the structure according to the present invention which is a unit consisting of a substrate 5, a block 7 and a glass substrate 6. In FIG. 3, a space 10 is held in common by the top ends 3Ab and 3Bb of tubes 3A and 3B formed in respective wells. The whole apparatus is filled up with a liquid not affecting chemotaxis such as a buffer solution. The amount of the liquid is sufficient for at least filling up a part of the space 10. Owing to this liquid, the whole apparatus is maintained under a definite pressure. Moreover, the resistance of the liquid contributes to the prevention of rapid migration of a sample caused by the injection pressure and horizontal off balance of the wells. FIG. 4 shows another example of the structure according to the present invention. In this unit, wells are provided with tubes 3A and 3B for injecting a sample and, further, tubes 4A and 4B connected thereto and a space 10 is provided by the top ends 3Ab, 4Ab, 3Bb and 4Bb of all of these tubes in common.

In the step of collecting the migrated cells by sucking from a well holding the specimen through a tube formed in the well, the inner pressure is reduced and thus the samples in wells are mixed each other. In the structure as shown by FIG. 4, this phenomenon can be particularly effectively relieved.

In case of detecting chemotaxis of cells or separating cells, it is preferable that the injected cells are first brought together in the vicinity of a channel in a well. In case of the apparatus for detecting chemotaxis of cells or separating chemotactic cells as shown by FIG. 3, for example, it is preferable that cells injected into the well 2A through the tube 3A are located in the vicinity of the channel 1. Namely, these cells may be considered as an example of a sample whose position in a well should be adjusted. This position adjustment can be carried out by sucking an appropriate amount of the liquid at an appropriate speed from the well 2B located oppositely across the channel through the tube 3B. The amount of the liquid to be sucked is determined based on the capacities of the tube and the well after discharging the liquid from the space 10. The amount of the liquid to be sucked and the sucking speed can be easily controlled by a computerized program.

Figure 5:
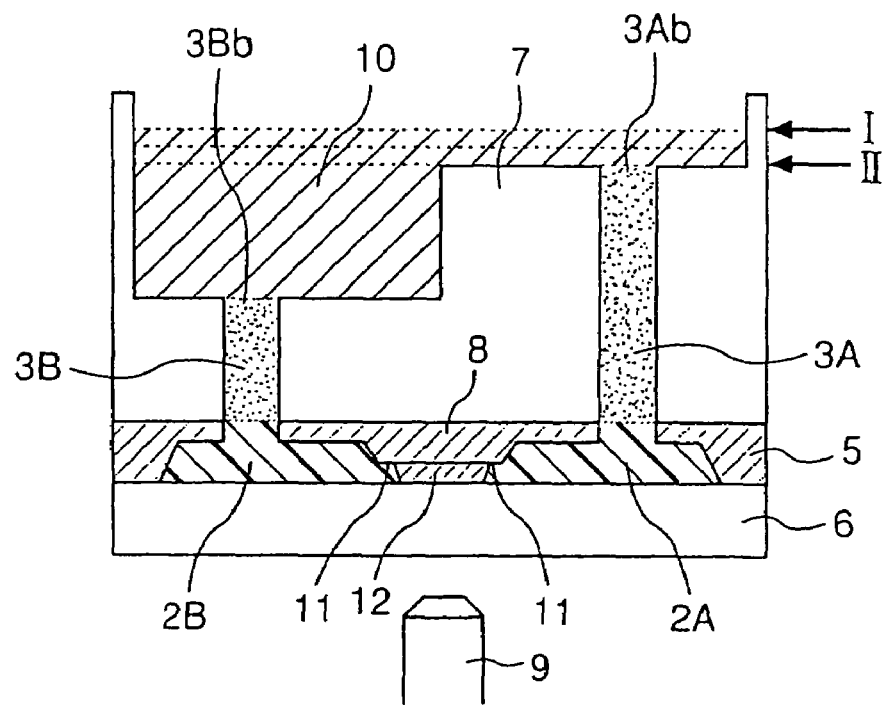
FIG. 5 is a model view showing another example of the application of the structure according to the present invention to an apparatus for detecting chemotaxis of cells or separating chemotactic cells wherein the top end 3Ab of a tube 3A in a well 2A for holding cells is located upper than the top end 3Bb of a tube 3B in another well 2B. The arrows I and II show the liquid levels of a liquid filling up the apparatus.
Figure 6:
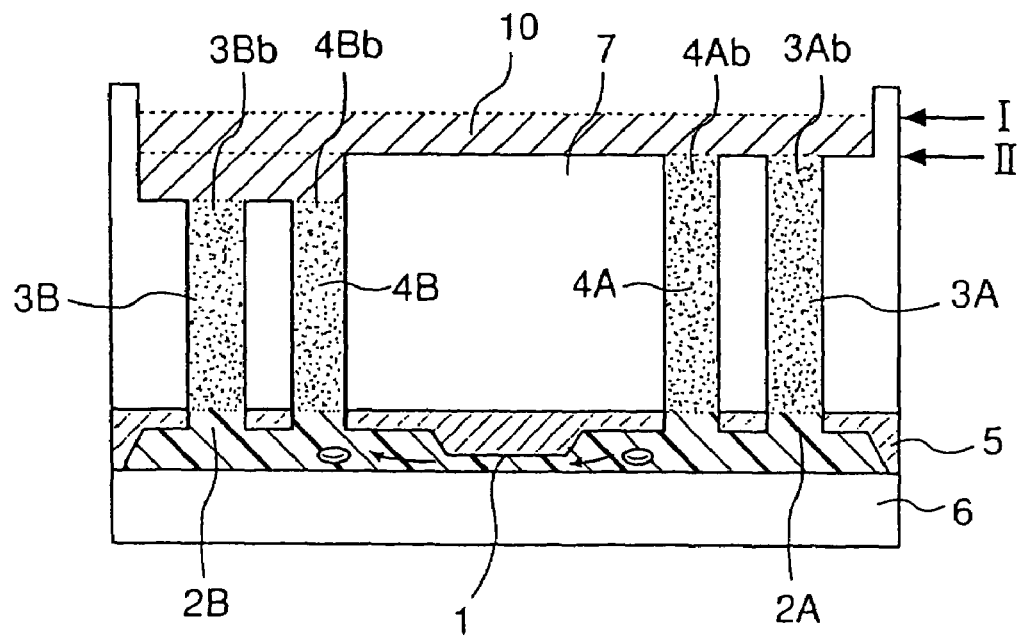
FIG. 6 is a model view showing another example of the application of the structure according to the present invention to an apparatus for detecting chemotaxis of cells or separating chemotactic cells which is provided with tubes 3 for injecting/collecting a sample into wells and tubes 4 for relieving decrease/increase in pressure at the step of injecting/collecting the sample, wherein the top ends 3Ab and 4Ab of tubes 3A and 4A in a well 2A for holding cells are located upper than the top ends 3Bb and 4Bb of tubes 3B and 4B in another well 2B. The arrows I and II show the liquid levels of a liquid filling up the apparatus.
Figure 7:
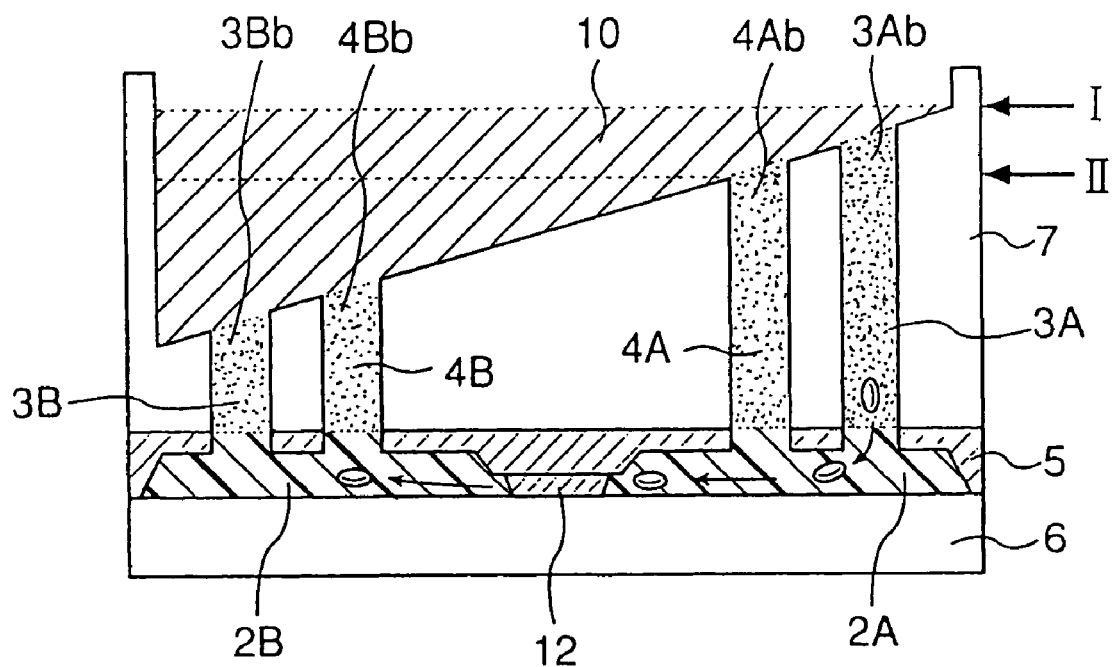
FIG. 7 shows a modification example of the structure as shown by FIG. 6. The arrows I and II show the liquid levels of a liquid filling up the apparatus.

The present invention further involves in its scope, as a modification of the above-described structure, a microsample treatment apparatus such as an apparatus for detecting chemotaxis of cells having a structure wherein the top end of a tube formed in a well for holding, for example, a cell suspension is located upper than the top end of a tube formed in another well opposite thereto across a channel (see FIGS. 5 to 7). In FIG. 5, a block 7 having a tube mounted thereon has been cut downward around the top end 3Bb of a tube 3B formed in a well 2B. Thus, the top end 3Ab of the tube 3A in a well 2A is located upper than the top end 3Bb of the tube 3B. At first, the amount of a liquid filling up the whole apparatus is controlled so that the liquid level is located above the top end 3Ab of the tube 3A, i.e., the position indicated by the arrow I in the figure. When cells are injected into the well 2A through the tube 3A in this state, rapid migration of the cell is prevented due to the uniform pressure in the whole apparatus and the resistance of the liquid. Thus, the cells scatter in the tube 3A and the well 2A. Next, the liquid is sucked off from the space 10 so that the liquid level is lowered to the position indicated by the arrow II (i.e., such a level as making the tope end 3Ab of the tube 3A visible above the liquid face3A). Further, an appropriate amount of the liquid is sucked off and thus the cells scattering in the vicinity of the channel in the well 2A can be brought together. The amount of the liquid to be sucked off can be calculated based on the capacities of the tube 3A and the well 2A. In usual, the object can be achieved by sucking off the liquid in an amount 1/10 to 1/3 times as much as the capacities. By injecting the specimen solution into the well 2B after returning the liquid level to the position indicated by the arrow I, a rapid change in pressure at the injection can be relieved.

As the liquid employed for returning the liquid level to the position indicated by the arrow I, it is preferable to use a liquid having a lower specific gravity than the liquid preliminarily contained in the apparatus (e.g., an aqueous solution such as a buffer solution). Thus, the upper part of the tubes in each well can be covered with the liquid having the lower specific gravity and thus the unnecessary diffusion of the sample can be prevented owing to the covering effect. An arbitrary liquid can be selected therefor so long as it is inert to the sample, insoluble in water and has a specific gravity lower than 1.0. Examples thereof include Mineral Water M3516 (specific gravity: 0.84, manufactured by Sigma) and liquid paraffin.

FIG. 6 shows an example of a unit having tubes 3A and 3B for injecting a sample and tubes 4A and 4B connected thereto in each well, wherein the top ends 3Ab and 4Ab of the tubes in a well 2A are located upper than the top ends 3Bb and 4Bb of the tubes in another well 2B. FIG. 7 shows an example wherein a slope is formed on a block 7 so that the top ends of tubes in a well 2A are located upper. These figures show the examples wherein the top ends of some tubes are located upper than the top ends of other tubes. Various modifications can be further made to achieve the same object.

Figure 8:
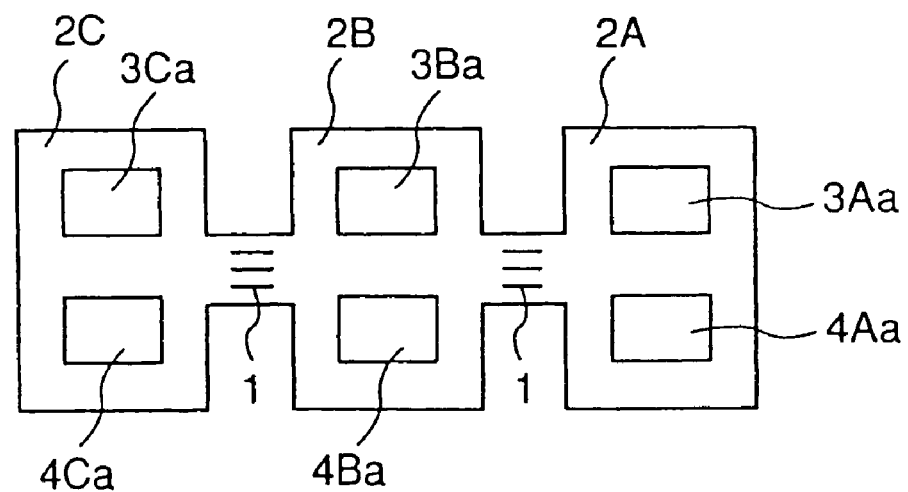
FIG. 8 is a top plan view of a substrate in an example wherein wells are connected each via a channel in the triple system.

The above-described structure wherein the top ends of some tubes are located upper than the top ends of other tubes is effective in the connecting manners as will be described hereinbelow. If necessary, other unit(s) may be further jointed and connected to a double system for connecting wells each via a channel as shown by FIGS. 3 to 7 to thereby give, for example, a triple system shown by FIG. 8. In FIG. 8, for example, cells are put into a well 2A, a chemotactic factor is put into a well 2C and a specimen solution is put into a well 2B. Thus, it can be examined whether or not the specimen solution inhibits the chemotactic factor. Moreover, multiple systems are applicable to various purposes.

Figure 9:
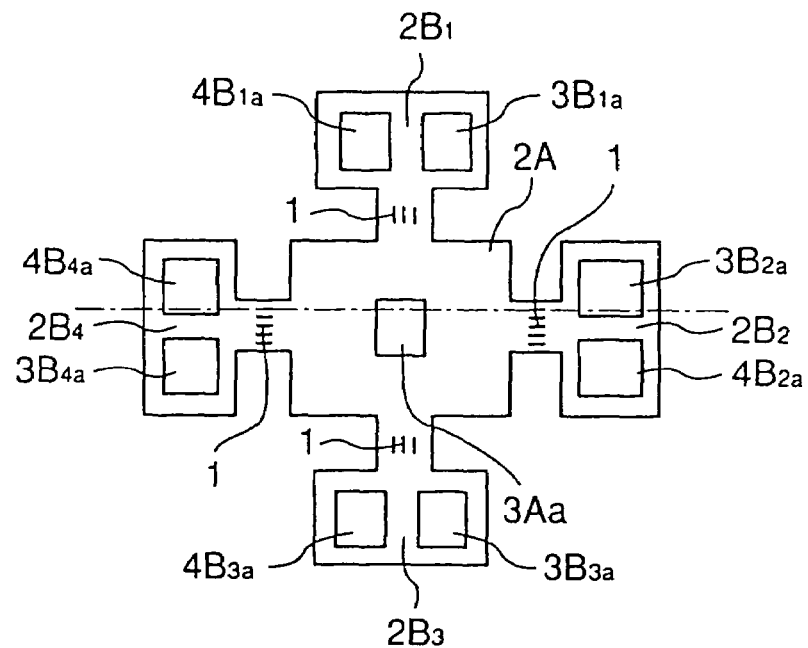
FIG. 9 is a top plan view of a substrate in an example wherein a plural number of wells $2B_{1-4}$ are connected to a single well 2A each via a channel 1.
Figure 11:
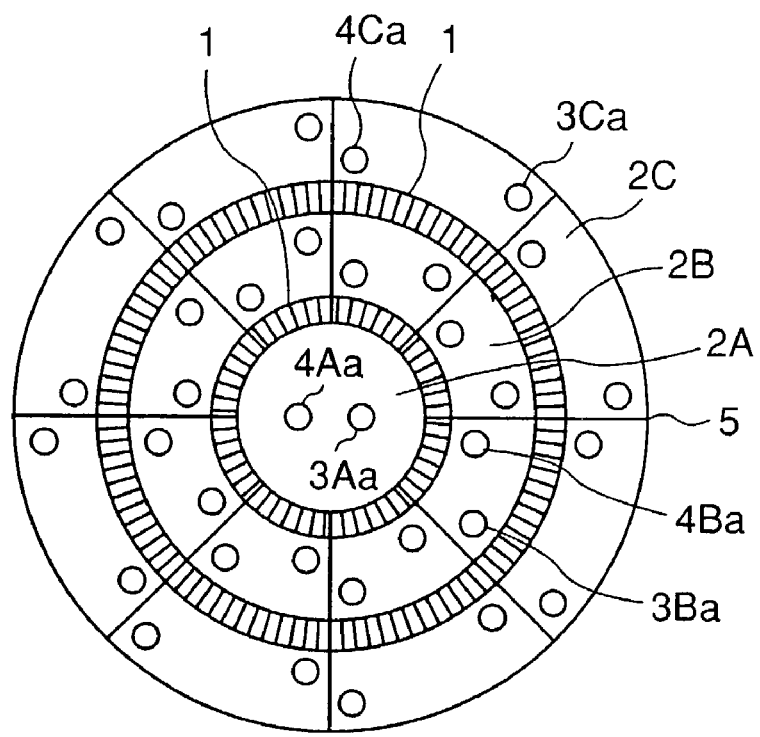
FIG. 11 is a top plan view of an example wherein the connection system in FIG. 9 is provided circularly.

As FIG. 9 shows, it is also possible to construct a so-called concentric system wherein a plural number of wells are connected to each other each via a channel around a single well. Furthermore, a concentric circular system as shown by FIG. 11 may be constructed as a modification of the type of FIG. 9. Although a triple system is employed in the example of FIG. 11, it is also possible to employ a double system. In the example of FIG. 9, a tube 3A is mounted to a penetrating hole 3Aa. Similarly, tubes $3B_{1-4}$ are mounted to penetrating holes $3B_{1a-4a}$ while tubes $4B_{1-4}$ are mounted to penetrating holes $4B_{1a-4a}$ respectively. A cell suspension is supplied into a well 2A through the tube 3A and various specimens are supplied into wells $2B_{1-4}$. Thus, a plural number of chemotactic factors can be examined at the same time. By supplying a sample containing a plural types of cells, the cells can be separated depending on types at once (i.e., sorting). For example, chemotactic factors corresponding to respective cell types are put into the wells $2B_{1-4}$ and a sample containing plural types of cells (for example, whole blood) is supplied into the central well 2A. Then the cells contained in the sample migrate toward the wells $2B_{1-4}$ containing the corresponding chemotactic factors. After a definite period of time, the cells are collected from each of the wells $2B_{1-4}$ through the tubes $3B_{1-4}$ or cells having migrated into the wells $2B_{1-4}$ are identified.

Figure 10:
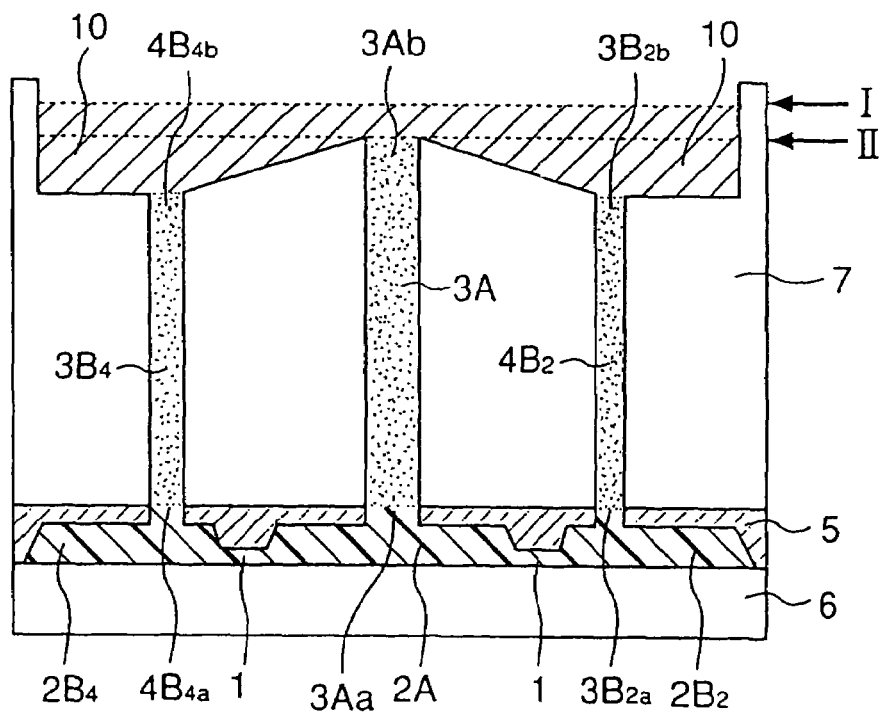
FIG. 10 is a sectional view of an apparatus having the substrate as shown by FIG. 9 along the dashed dotted line in FIG. 9. The arrows I and II show the liquid levels of a liquid filling up the apparatus.

In the well-connecting manners as shown by FIGS. 8, 9 and 11, the tubes 3 and 4 are connected to each other in the well 2 in which they are provided. In these connecting manners, all of the tubes hold at the top ends thereof a space 10 in common. The top ends of the tubes in a well into which cells are injected are located upper than the top ends of other tubes. Then a liquid is supplied so that the top ends of the tubes in the well into which cells are injected are submerged (see FIG. 10). FIG. 10 is a sectional view of the apparatus shown by FIG. 9 along the dashed and dotted line. In this example, the top ends 3Ab and 4Ab of tubes 3A and 4A in a well 2A are located upper than the top ends $3B_{1b-4b}$ of tubes $3B_{1-4}$ in other wells $2B_{1-4}$. An arrow I shows that the level of the liquid filling up the space 10 is located above the top ends 3Ab and 4Ab of the tubes 3A and 4A. Cells injected into the well 2A through the tube 3A scatter in the tube 3A and the well 2A. Then the liquid in the space 10 is sucked off and thus the liquid level is lowered to the position indicated by another arrow II so that the top end 3Ab of the tube 3A becomes visible above the liquid face. Then an appropriate amount of the liquid is further sucked off. Thus, the cells in the well 2A can migrate toward the wells $2B_{1-4}$ and thus are brought together in the vicinity of the channel 1 toward respective wells. The amount of the liquid to be sucked off can be calculated based on the capacities of the tube 3A and the well 2A. Thus, the chemotaxis of the cells in the well 2A concerning the wells $2B_{1-4}$ can be examined under the same positional conditions.

Figure 21:
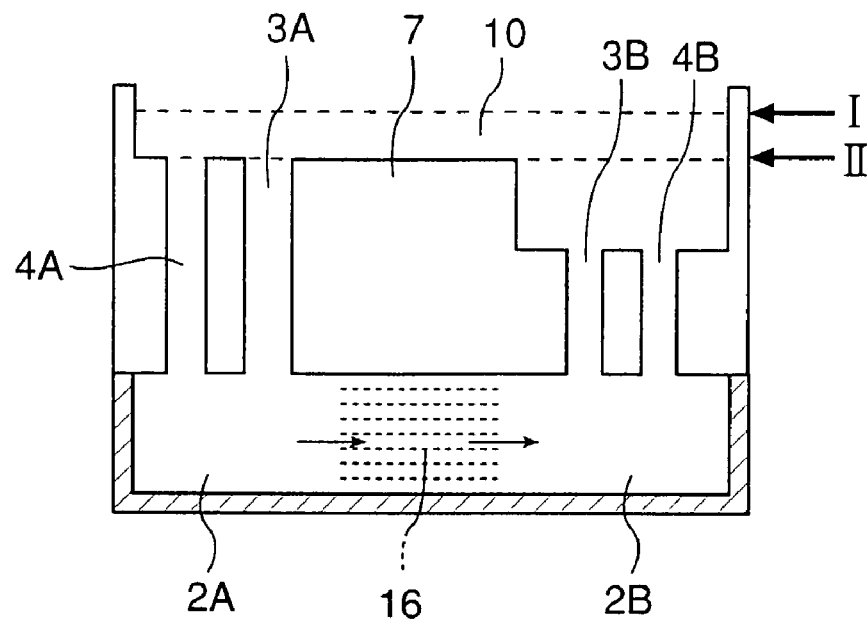
FIG. 21 is a model view of an apparatus wherein a well to be reacted and another well for holding the target substance are connected via a column. The arrows I and II show the liquid levels of a liquid filling up the apparatus.

As another example of the embodiment to which the structure of the present invention can be applied, an apparatus shown by FIG. 21 may be cited. Namely, FIG. 21 is a model view of an apparatus wherein a reaction is carried out in a well 2A followed by a treatment through a column 16 and then unadsorbed substances passing through the column are collected from a well 2B. In this case, the column serves as an obstacle having resistance to fluids. Substances to be reacted are put into the well 2A in the state that the liquid level is at the position indicated by an arrow I. After the completion of the reaction, the liquid level is lowered to the position indicated by another arrow II. After further sucking, the reaction mixture migrates from the well 2A toward the column 16. By further sucking, a substance passing through the column migrates toward the well 2B. In case where the substance adsorbed by the column is the target substance, the eluate is supplied into the column via the well 2A. Thus, the eluted substance can be collected in the well 2B.

In addition to the above-described case, various applications can be made. That is to say, interactions among substances can be examined at the level of microquantities by controlling the migration of samples among wells which are connected to each other. For example, these apparatuses are applicable to antigen/antibody reactions, enzyme/substrate reactions, reactions between soluble receptors and ligands, and so on.

In the well 2A of the apparatus shown by FIG. 5, for example, an antibody bonded to plastic beads of a definite size is reacted with an antigen protein. Then the liquid level is lowered from I to II and further the liquid is sucked off. Thus the unreacted antigen protein passes through the groove in the barrier 12 and migrates into the well 2B. However, an antigen which has reacted with the antibody bonded to the plastic beads cannot pass through the groove in the barrier 12 because of the presence of the beads, thereby being separated from the unreacted antigen protein. Thus, substances can be separated by appropriately selecting the combination of the bead size and the groove width.

It is also possible to use magnetic beads. For example, magnetic beads having a uniform particle size, which are composed of polymer cores having a magnetizable substance (for example, $\gamma Fe_2O_3$, $Fe_3O_4$) uniformly distributed therein and a hydrophilic polymer coating, are commercially available (Dynabeads® manufactured by DYNAL, Norway). By bonding various antibodies onto the surface of these beads, the magnetic beads can be bonded to cells or proteins. By bringing close to a powerful magnet (MPC), the magnetic beads are magnetized and attracted to the magnet. When the magnet is moved away, the beads are demagnetized and thus scatter again. These characteristics have been used in purifying cells, proteins, etc. For example, Kanegasaki, S. et al. isolated peripheral B lymphocytes by using magnetic polystyrene beads (manufactured by DYNAL) coated with CD19 antibody (J. Biochem., 117:758-765 (1995)).

Figure 22:
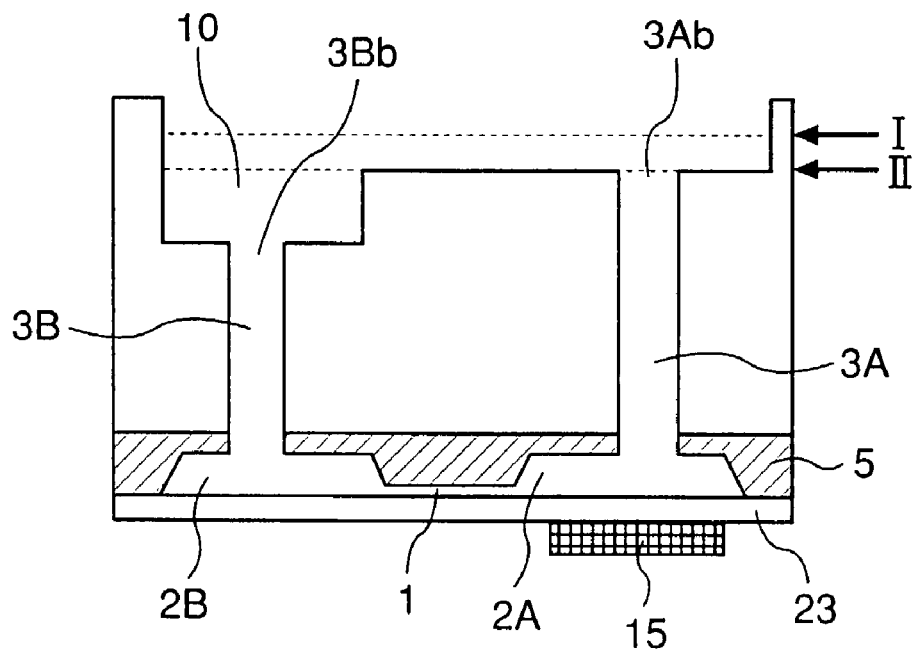
FIG. 22 is a model view of an apparatus for separating substances. The arrows I and II show the liquid levels of a liquid filling up the apparatus.

In an apparatus shown by FIG. 22, a protein mixture and antibodies labeled with magnetic beads (magnetic antibody beads) are injected into a well 2A at the liquid level I. After adsorbing a protein reacted with the antibody by a magnet 15 provided at the bottom of the well 2A, the liquid level is lowered to II. Then the liquid is sucked off from a space 10. Thus, a protein unadsorbed by the magnet 15 alone migrates into another well 2B. By selecting an appropriate antibody, a desired protein can be thus separated or an unnecessary protein can be thus eliminated. For separate proteins with the use of magnetic materials, it has been a practice to use columns. However, treatments with columns can be performed on the milliliter scale and, therefore, are unsuitable for treating proteins in microquantities. By using the apparatus according to the present invention, proteins can be separated even on the scale of several microliters or less.

The present invention makes it possible to downsize the whole apparatus and thus samples can be treated in microquantities. Moreover, it is possible to integrate multiplicity of units and thus a large number of specimens can be treated at the same time. In addition, the treatment can be easily automated by programmed control of suction and injection of liquids.

That is to say, the apparatus can be automated by providing a unit part having a single unit, an integration unit having a plural number of units of the same or different types or a plural number of integration units, liquid level control pipette(s) and a system for controlling the movements of the liquid level control pipette(s). The operations of the liquid level control pipette(s) are controlled as follows. Namely, a definite amount of a liquid, which is contained in the space held by the top ends of a plural number of tubes in common in each unit, is sucked by the liquid level control pipette(s) to thereby adjust the position of a sample in the well, or transfer the sample into the next well and, if necessary, the liquid in the compensatory amount is supplied from the liquid level control pipette(s) into the space to thereby return the liquid face to the original level. These controlling operations can be easily carried out by computerized programming.

It is also possible to automate the whole apparatus involving the steps of supplying and collecting a sample, a specimen, a reagent, etc. by providing a unit part, a sample reservoir, a specimen reservoir and sample supply pipette(s) and specimen supply pipette(s) movable over these parts and further a system for controlling the operations of these pipettes. If necessary, it is also possible to add a pipette washing part and a system for controlling the operation of washing the pipettes in the pipette washing part.

Next, the structure of the apparatus according to the present invention will be described in greater detail by reference to an apparatus for detecting chemotaxis of cells as an example. However, it is to be understood that the present invention is not restricted to an apparatus for detecting chemotaxis of cells but applicable to other apparatuses in order to solve similar technical problems as discussed above.

1) Structure of Unit

As FIG. 3 shows, a channel 1 and wells 2A and 2B are integrally formed on a substrate 5. The substrate 5 has holes (penetrating holes) 3Aa and 3Ba for mounting tubes 3A and 3B connected to respective wells. A block 7 having the tubes 3A and 3B is fixed so as to fit for the penetrating holes 3Aa and 3Ba. In the upper part of the block, a space 10 commonly held by the top ends 3Ab and 3Bb of the tubes 3A and 3B is provided. The bottom face of the substrate 5 is adhered to an optically polished glass substrate 6. The block 7, the substrate 5 and the glass substrate 6 may be pressed and fixed by fastening, for example, with an O-ring or a packing (see FIG. 20). Alternatively, the substrate 5 and the glass substrate 6 may be integrally formed. Alternatively, the substrate 5, the glass substrate 6 and the block 7 may be integrally formed. As FIG. 4 shows, the tubes formed in the wells 2A and 2B may be further provided with tubes 3A, 3B, etc. for injecting/collecting a sample and tubes 4A, 4B, etc. for relieving pressure changes. As FIGS. 5, 6. etc. show, the space 10 may be partly cut downward to form a concave. Alternatively, a slope may be formed as shown by FIG. 7, etc.

2) Well

Figure 24:
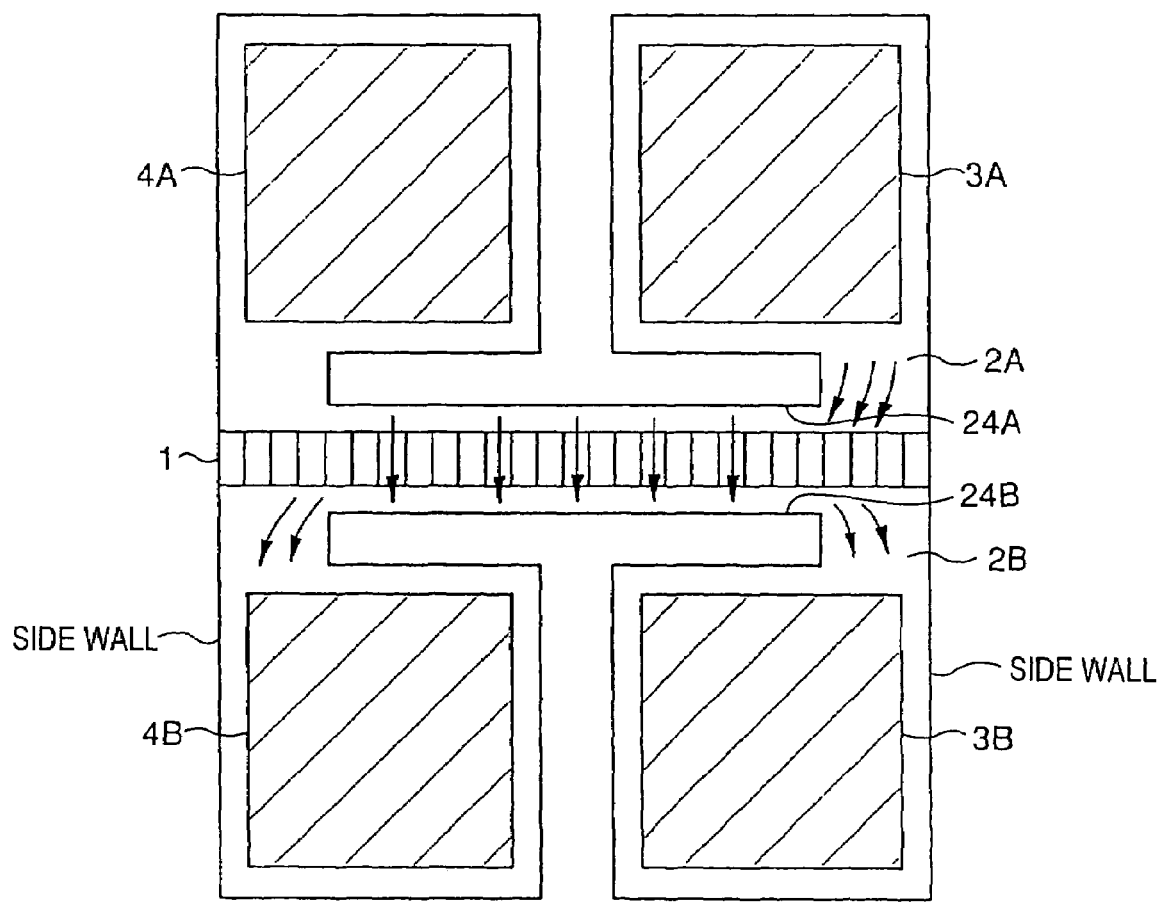
FIG. 24 shows an example of wells wherein walls are formed along a channel.

Wells 2 are formed for holding a sample (i.e., a cell suspension) or a specimen solution such as a solution containing a chemotactic factor or a solution containing an inhibitor therefor. The capacity of the wells is not particularly restricted, so long as a liquid can be held therein in the minimum amount needed. For example, it is sufficient that the depth ranges from about 0.05 to about 0.1 mm, the width is about 1.2 mm and the length is about 2.5 mm. It is also possible to provide a wall orthogonal to a channel in one or both of wells connected to each other via the channel (for example, the well for holding cells) to thereby restrict the amount of the liquid in the vicinity of the channel. Thus, the position of cells in the well can be adjusted (FIG. 24). FIG. 24 shows an example wherein wells 2A and 2B are connected to each other via a channel 1 and walls 24A and 24B are formed in respective wells orthogonally to the channel 1. Although the distance between the walls 24 and the channel 1 may be arbitrarily determined, it usually ranges from 50 to 300 µm.

Figure 25:
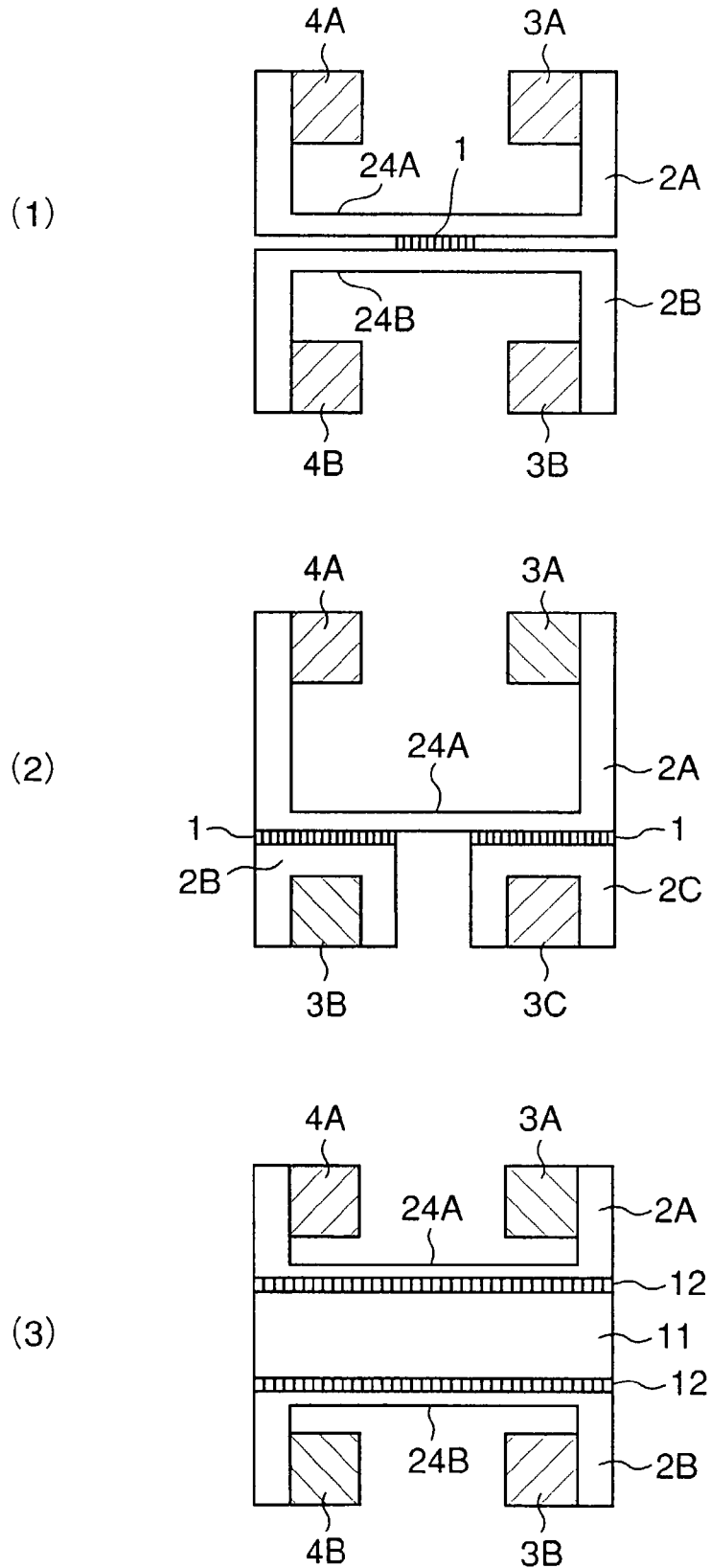
FIG. 25 shows another example of wells wherein walls are formed along a channel.

FIG. 25 shows modification examples of the well unit having walls provided orthogonally to the channel. That is, FIG. 25(1) shows an example wherein a channel is formed in a part of the well width; (2) shows an example wherein a channel is halved at the center, a couple of wells (2B, 2C) are provided opposite to a single well (2A) across the channel, and a wall 24 is formed exclusively in the well 2A side; and (3) shows an example wherein two arrays of barriers are formed in both sides of a terrace 11 in a channel. Needless to say, these modifications are cited merely by way of example and thus the present invention is not restricted thereto. If necessary, a terrace may be formed between the wall provided orthogonally to the channel and the bank.

3) Channel

Figure 12:
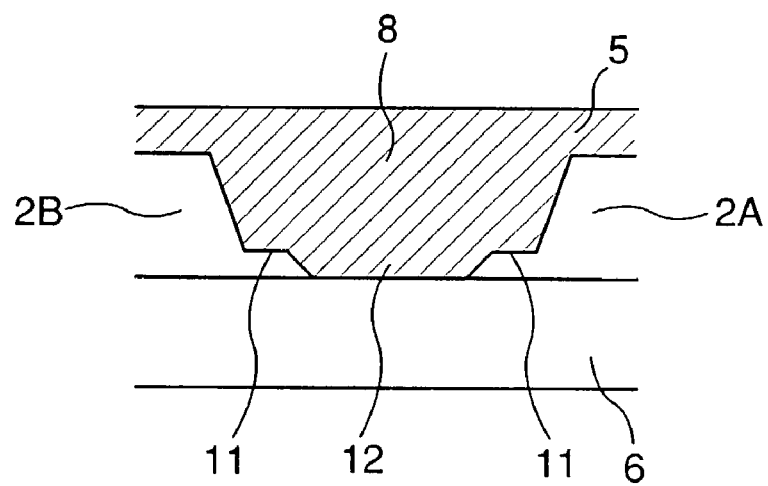
FIG. 12 shows an example of the structure of a channel 1.

Now, an example of the structure of a channel 1 (FIGS. 1, 3 and 4) will be illustrated by reference to FIG. 12. The channel 1 is a space provided between a bank 8 (a convex on a substrate 5) partitioning wells 2A and 2B at both ends and a glass substrate 6. The bank 8 partitioning the wells 2A and 2B formed at both ends of the channel 1 is not restricted in size. For example, the height of the bank 8 may range from about 0.03 to about 0.1 mm, while the length in the direction toward the opposite well may range from about 0.01 to about 0.5 mm and the length in the direction orthogonal to the direction toward the opposite well may be about 1.2 mm.

Figure 13:
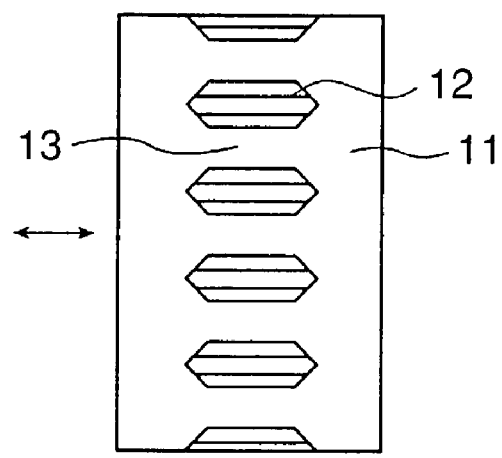
FIG. 13 shows an example of the arrangement of barriers 12 and grooves 13 in a channel 1. The arrow shows the direction toward the opposite well.
Figure 14:
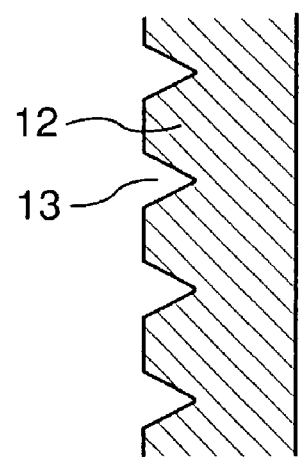
FIG. 14 is a sectional view of the channel 1 shown by FIG. 13.
Figure 15:
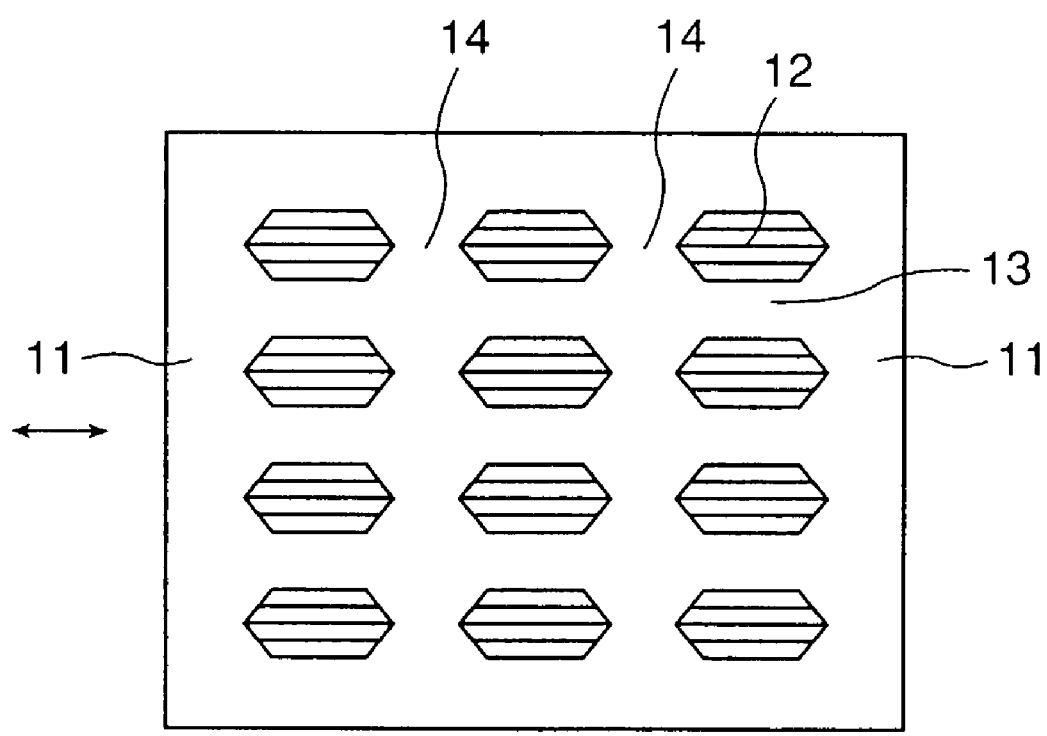
FIG. 15 shows an example wherein grooves 13 in the direction toward the opposite well across a channel 1 are connected via two grooves 14 orthogonal thereto. The arrow shows the direction toward the opposite well.

In a preferred embodiment, a plural number of barriers 12 are formed on the bank to thereby constitute grooves 13 through which cell pass, as shown by FIGS. 13 to 15. In case where no barrier constituting grooves is formed in the upper part of the bank, a terrace providing a gap or a depth fit for the diameter or deformability of cells is formed between the upper face of the bank and the glass substrate. In this case, the depth usually ranges from 3 to 50 µm depending on the type of cells. That is to say, the width may range from 3 to 10 µm (for example, 4, 5, 8 or 10 µm) in case of neutrophils, eosinophils, basophils, monocytes/macrophages, T cells, B cells and the like, and from 8 to 20 µm in case of cancer cells and cells existing in tissues.

By forming flat terraces in both sides of the barriers on the upper face of the bank, the passage of cells can be more easily observed. Thus, it is favorable to form terraces 11 (FIG. 12), though they are not essentially required. In case of providing the terraces 11, the length thereof in the direction toward the opposite well appropriately ranges from about 0.01 mm to about 0.5 mm.

Figure 23:
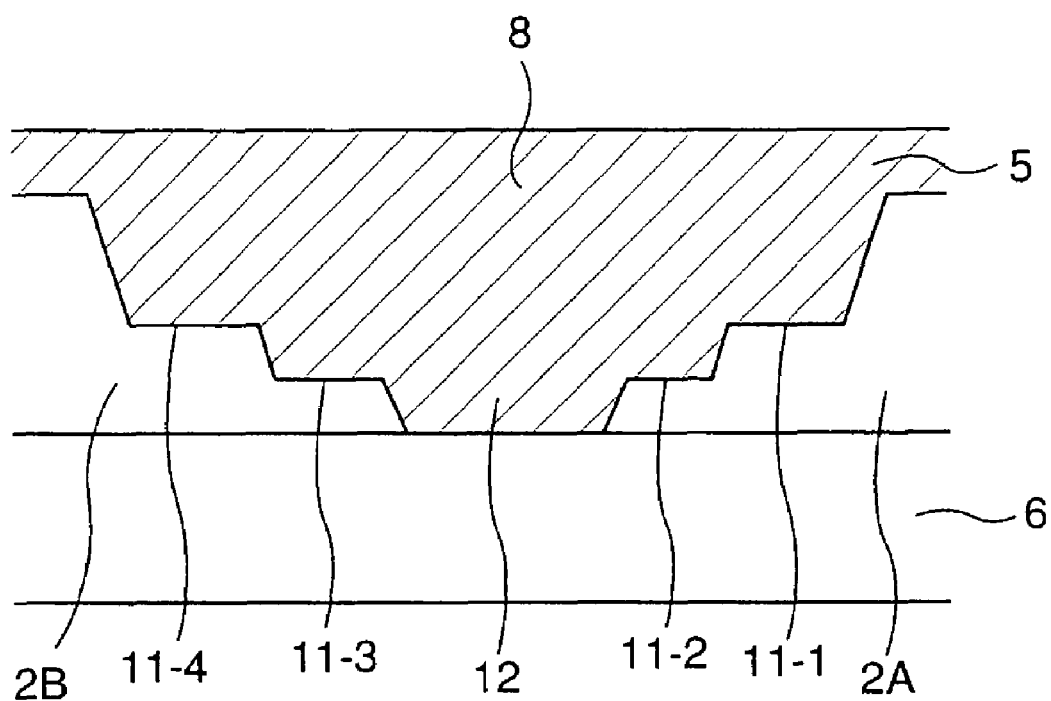
FIG. 23 shows an example wherein a bank 8 in a channel 1 has multistage terraces $11_{-1-4}$.

By forming multistage terraces 11 as FIG. 23 shows, cells put into wells in one side can be easily brought together in the vicinity of the bank 8 by sucking from the other side to adjust the position of the cells in the well. In case where the cells are neutrophils, eosinophils, basophils, etc., for example, the distance between the terraces $11_{-2}$ and $11_{-3}$ and a glass substrate 6 (i.e., corresponding to the height of a barrier 12 in the figure) is set to 3 µm and the distance between the terraces $11_{-1}$ and $11_{-4}$ and a glass substrate 6 is set to 4.5 µm. Then cells are supplied into a well 2A and the liquid is sucked from the side of another well 2B. Then the cells once stop at the terrace $11_{-1}$. Next, the cells are liable to bring together between the terrace $11_{-2}$ and the glass substrate 6. The distance between each of the terraces $11_{-1}$ to $_{-4}$ and the glass substrate 6 can be arbitrarily determined depending on the sample to be treated. Although these distances usually range from about 3 to 5 µm, the present invention is not restricted thereto. When the terrace ($11_{-3}$) in the side opposite to the wells containing the cells is made about 1.5 to 5 times longer than the terrace ($11_{-2}$) in the side of the wells containing the cells, the cells having passed through the channel can be more easily observed and counted. Although a barrier 12 is formed in the example shown by FIG. 23, the barrier is not always necessary in case where the distance between the terraces $11_{-2}$ and $11_{-3}$ and the glass substrate 6 corresponds to the diameter or deformability of cells.

In case where barriers 12 (see FIGS. 12 to 14) are formed on the upper face of the bank, grooves 13 constituted by the barriers 12 may have an arbitrary cross-sectional shape, for example, a V-shaped section, a convex section or a semicircular section. It is preferable that the grooves 13 have a width fit for the diameter or deformability of cells. The term "deformability" of cells as used herein means that, in case of flexible cells, the cells can easily change their shape (for example, into flat or string-shaped cells) owing to the flexibility and thus can pass through a gap having a smaller size than the diameter of the cells being in the inherent spherical shape in a free space. By forming such grooves, cells can be observed at individual level and thus separated depending on desired types. The width of a groove 13 usually may range from 3 to 50 µm. It is preferable that the width allows the passage of cells one by one. Thus an appropriate width may be selected depending on the cell type. The width may range from 3 to 10 µm (for example, 3, 5, 8 or 10 µm) in case of neutrophils, eosinophils, basophils, monocytes/macrophages, T cells, B cells and the like, and from 8 to 20 µm in case of cancer cells and cells existing in tissues. The number of the grooves 13 is determined depending on the width of the barriers concerning the channel width and the groove width. In case where the channel width is 1 mm, the barrier width is 10 µm and the groove width is 5 µm, for example, the number of grooves is 66 at the largest. To smoothly perform the detection and observation, the number of the grooves 13 preferably ranges from 1 to about 100, still preferably from about 10 to about 70.

The length of the barriers 12 ranges from about 5 to about 400 μm. For example, use may be made of a barrier length of 5, 15, 20, 30, 40, 60, 100, 200, 300 or 400 μm. The width of the barriers 12 per se can be appropriately determined. In case of employing the structure as will be shown in FIG. 38 hereinafter, it is effective that the width and length of the barriers are almost the same.

Figure 36:
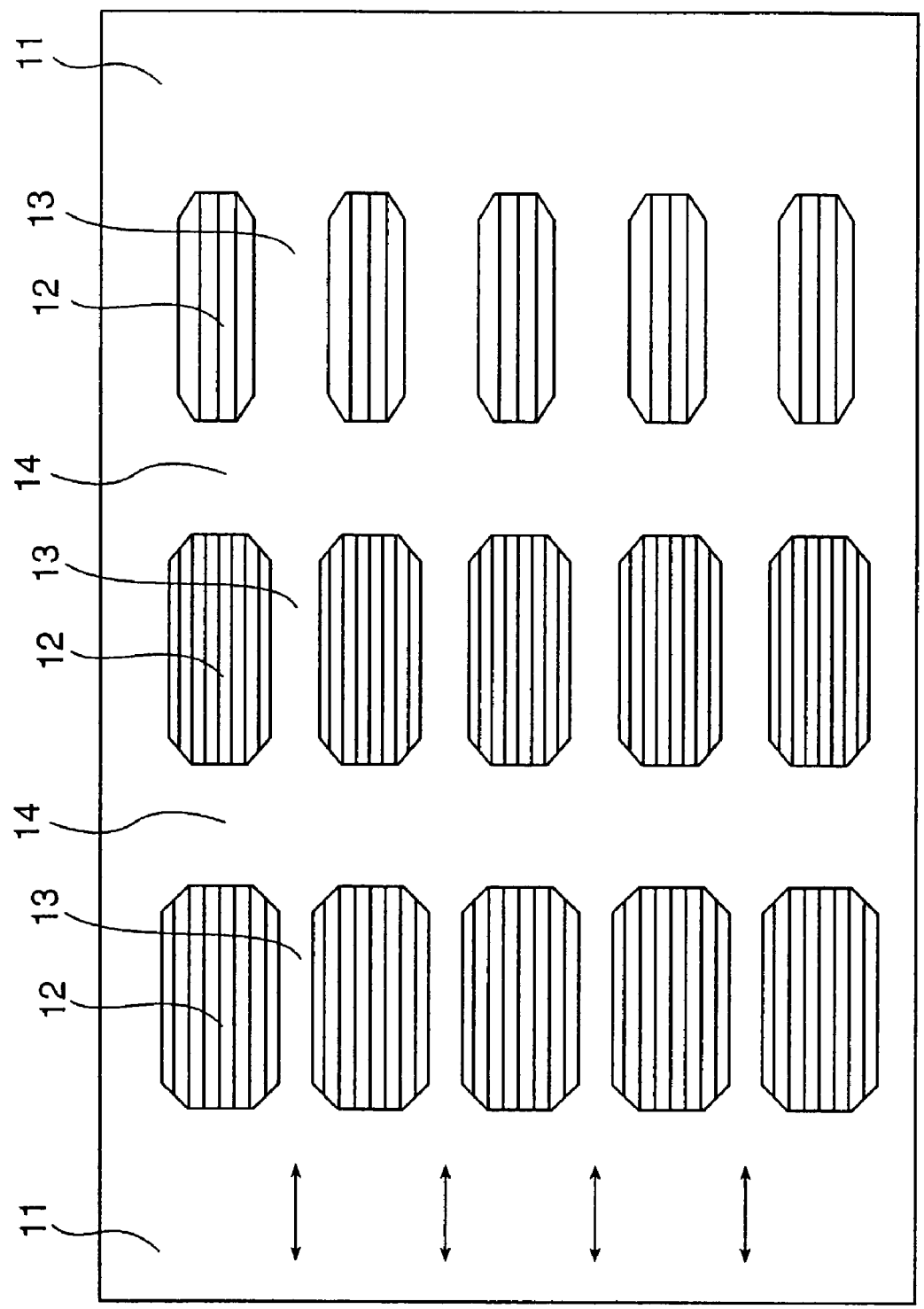
FIG. 36 shows an example wherein grooves in the direction toward the opposite well across a channel are connected to each other via two grooves formed orthogonally thereto and the width of the grooves in the direction toward the opposite well is changed stepwise each time the grooves intersect the grooves orthogonal thereto. Each arrow shows the direction toward the opposite well. In this figure, the width of the barriers per se is changed.
Figure 37:
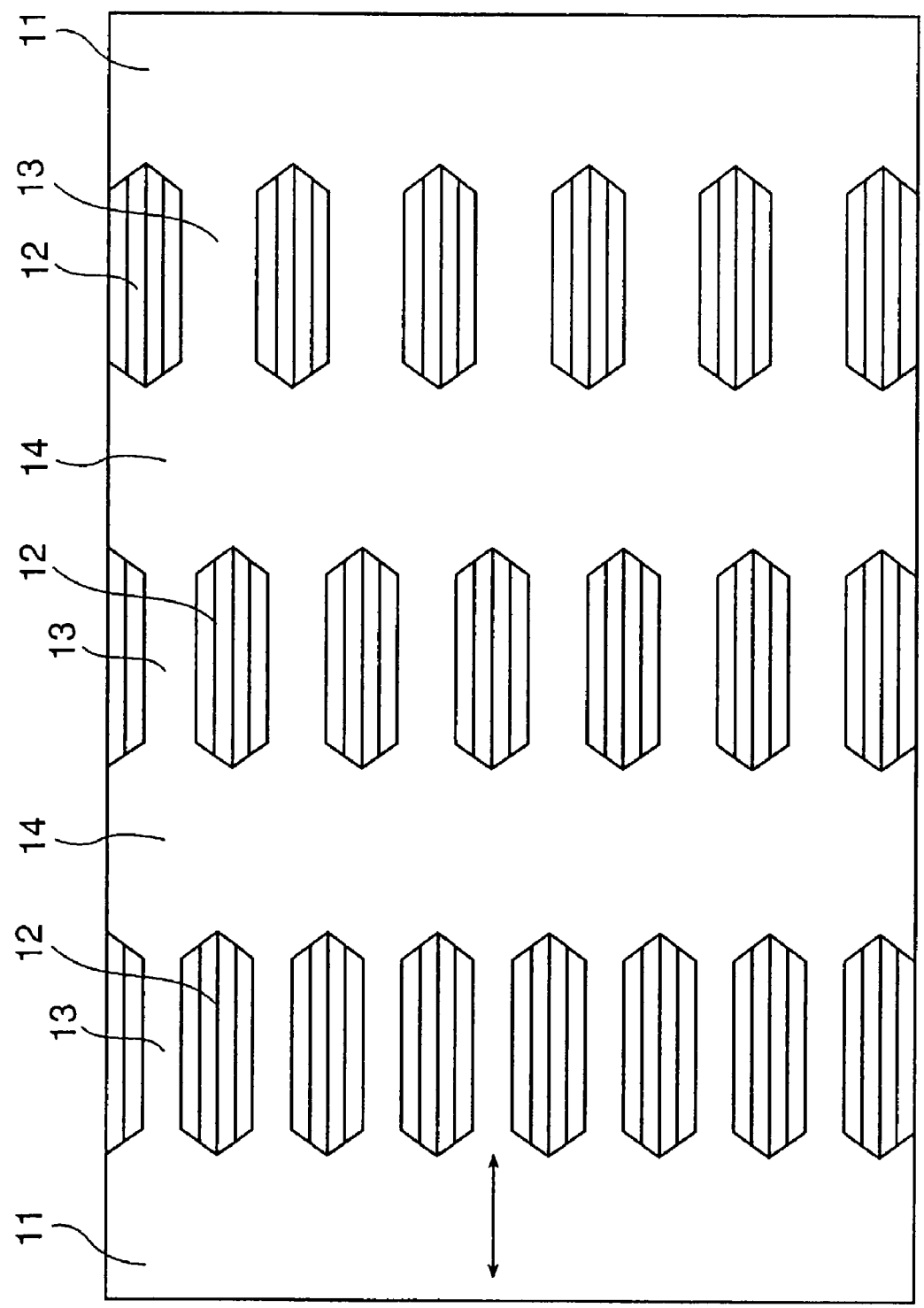
FIG. 37 shows an example of the modification of the structure of FIG. 36 in which the barriers have the same size but are changed in number. The arrow shows the direction toward the opposite well.
Figure 38:
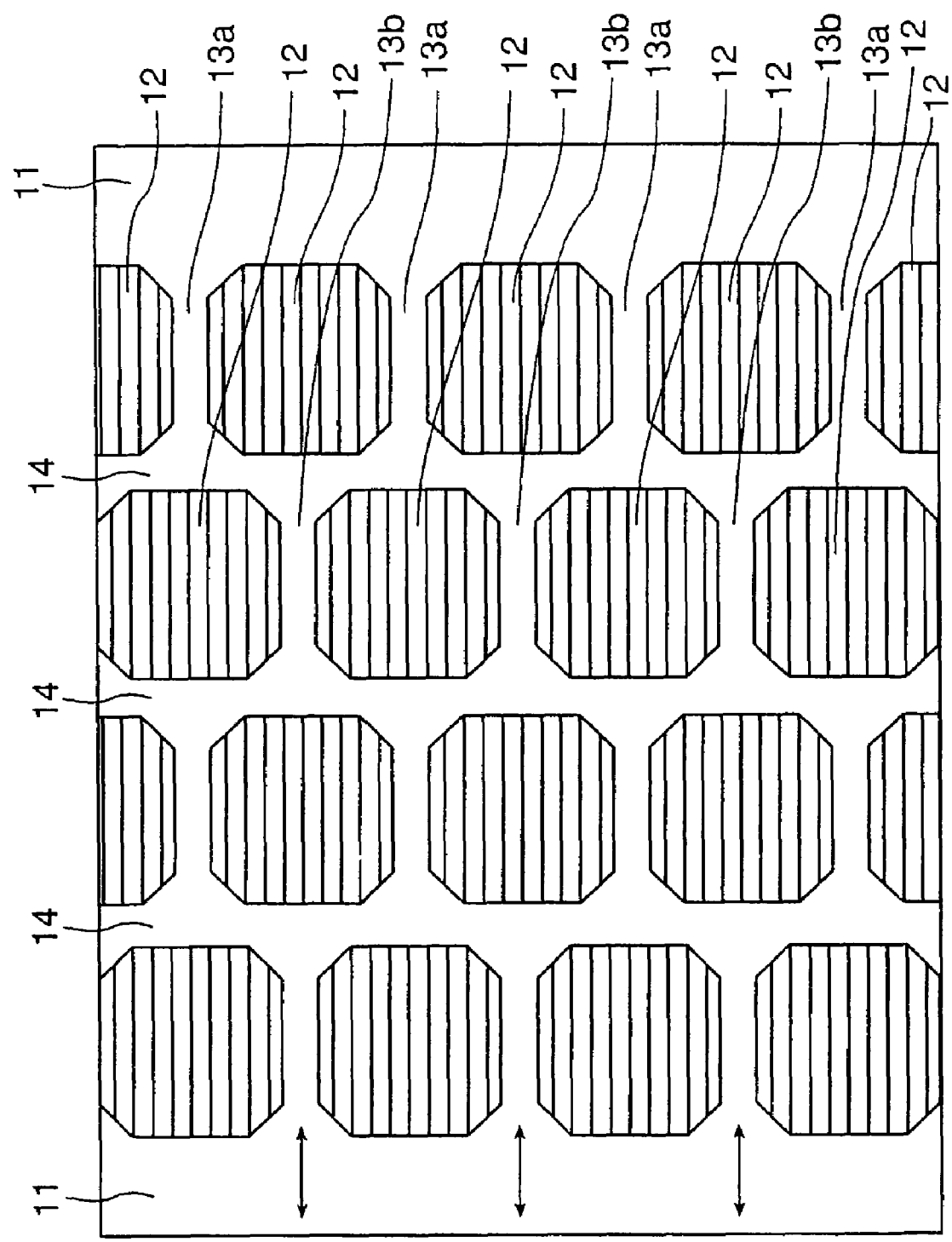
FIG. 38 shows an example wherein grooves in the direction toward the opposite well across a channel are connected to each other via three grooves formed orthogonally thereto and the grooves in the direction toward the opposite well are formed by mutually shifting the positions thereof each time the grooves intersect the grooves orthogonal thereto. In this figure, the grooves shift by ½ pitch toward the orthogonal direction. Each arrow shows the direction toward the opposite well.
Figure 39:
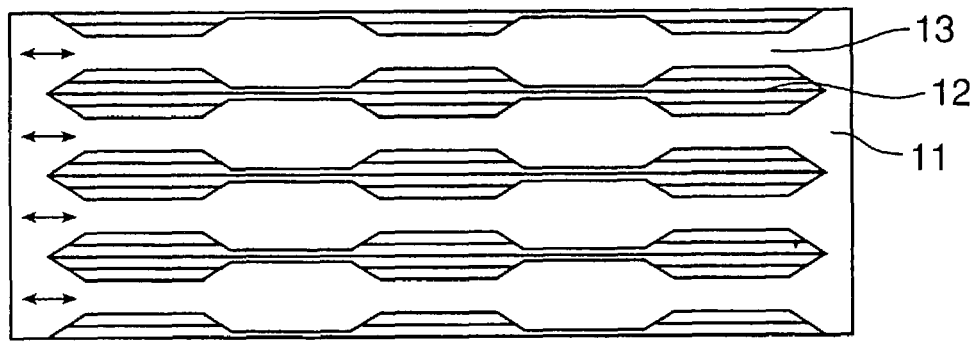
FIG. 39 shows an example wherein barriers are jointed in the direction toward the opposite well. Each arrow shows the direction toward the opposite well.
Figure 40:
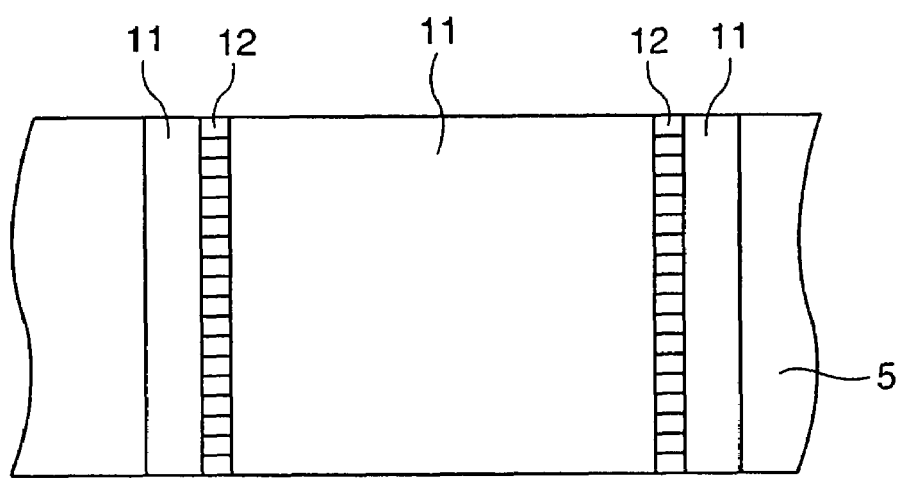
FIG. 40 shows an example wherein a terrace is formed at the center of a bank and two arrays of barriers are formed in both sides of the terrace.
Figure 40:
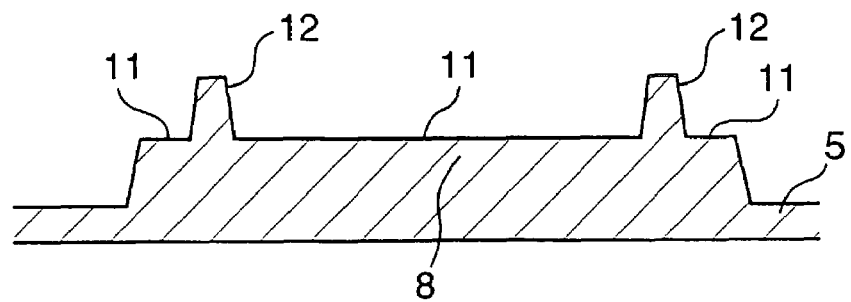

As FIG. 15 shows, the grooves 13 constituting the channel 1 may be connected to each other via one or more grooves 14 orthogonal to the direction toward the opposite well. Owing to this structure, the diffusion of a substance put into one well toward the other well can be uniformized, or cells under passage can be more accurately understood. In this case, the width of the grooves 13 may be changed stepwise each time the grooves intersect grooves 14 orthogonal thereto in the direction toward the opposite well (see FIGS. 36 and 37). Alternatively, grooves in the direction toward the opposite well may be formed by mutually shifting the positions thereof each time the grooves intersect grooves orthogonal thereto (see FIG. 38). FIG. 38 shows an example wherein the grooves are formed as shifting by ½ pitch in the orthogonal direction. It is also possible that the barriers are jointed to each other in the direction toward the opposite well (see FIG. 39). Alternatively, arrays of barriers can be formed in two positions in both side of a terrace which is formed at the center of the bank (see FIGS. 25(3) and 40). By using these structures, cells having passed the grooves can be easily observed and counted. It is desirable that the terrace located at the center has an area which can be included in the microscopic field. FIG. 40(1) is a top plan view while (2) is a sectional view.

The height of the barrier 12 (i.e., the depth of the grooves) may be appropriately determined depending on the depth of focus of the objective lens of a microscope, a CCD camera, etc. to be used in observing the cell migration. For example, a depth of about 3 to about 4.5 μm is preferable in case of an objective lens having a focus depth of 10 to 40× magnification, though the present invention is not restricted thereto.

4) Construction of Well and Channel

As a material of the substrate 5, it is preferable to use single-crystal silicon which can be easily fine processed and is relatively inert to cells. The barriers 12 and the grooves 13 in the channel 1 can be constructed by subjecting the single-crystal silicon to photolithography or etching (for example, wet etching or dry etching) employed in manufacturing integrated circuits. The wells 2 and the penetrating holes 3a and 4a, which are larger than the barriers 12 and the grooves 13, can be constructed by using various known engineering techniques such as sand blasting and dry etching. In addition to single-crystal silicon, use can be made of hard glasses, hard plastics, metals, etc., so long as a microstructure can be constructed in the channel. In case of using plastics, it is preferable to employ a treatment for making the surface hydrophilic, for example, forming a hydrophilic film on the surface. It is also possible to separately construct the channel 1 and the wells 2 and then combine them together.

5) Block and Tube

As shown by FIG. 3, the block 7 is a member located on the substrate 5 and having tubes connected to wells. The tubes usually have a square or circular cross-sectional shape. Although these tubes are not restricted in size, a square tube has a side length of about 1 mm while a round tube has a diameter of about 1 mm in usual. To hold a cell suspension or a specimen solution in a desired volume, it is necessary that these tubes have a length of about 2 to about 10 mm. The materials of the block or tubes maybe selected from among glasses, plastics such as acrylic resins and metals. The tubes can be easily produced by using commonly employed engineering techniques such as mechanical drilling or laser drilling. Similarly, the space held commonly by the top ends of the tubes can be formed above the block 7 by usual engineering techniques.

Figure 35:
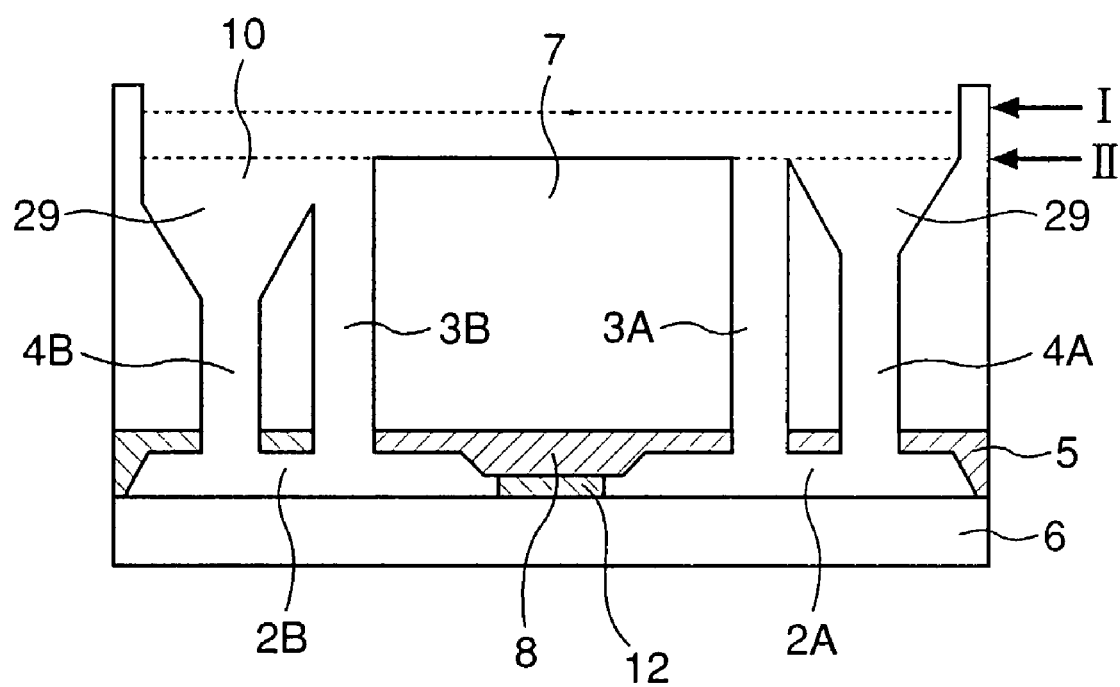
FIG. 35 shows an example wherein pipette tip inlets are formed in the upper part of tubes for injecting/collecting a sample.
Figure 35:
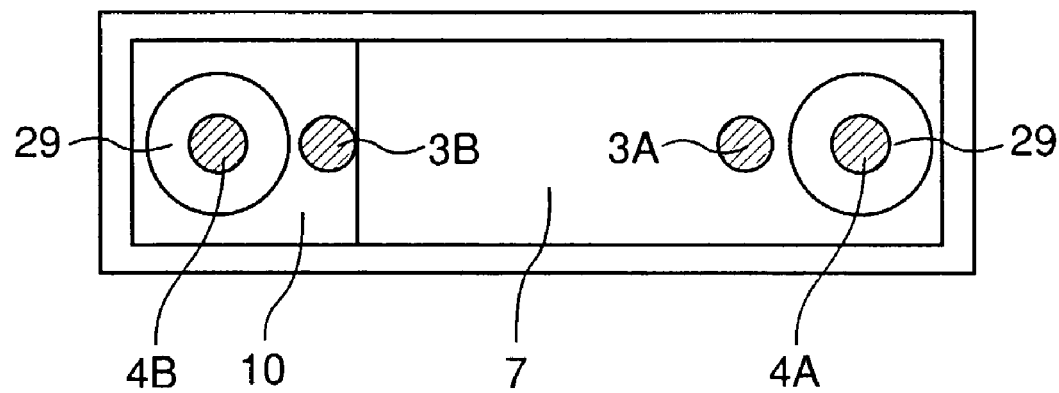

To inject cells or a specimen into each unit by hands (i.e., manually), the periphery of the top end of each supply tube may be cut downward to thereby form a funnel-shaped concave. Thus, a pipette can be easily inserted (29 in FIGS. 35(1) and (2)).

6) Glass Substrate

As shown by FIG. 3, the glass substrate 6 is tightly pressed on the substrate 5 to provide a space in which a liquid is held, thereby enabling the observation of cells passing through the channels. Thus, the glass substrate 6 should remain optically transparent and flat and provide a plane to which cells can adhere. Use can be made therefor of glass as well as plastics such as transparent acrylic resins, so long as the above objects can be achieved thereby. Although its thickness is not particularly restricted so long as no strain arises in the step of pressing onto the substrate, the thickness adequately ranges from 0.7 to 2 mm.

7) Arrangement of Multiplicity of Units

By referring a plural number of wells connected to each other each via a channel as a single unit, a plural number of units may be arranged and integrated on a single substrate. Thus, an apparatus whereby a large number of specimens can be treated at the same time can be obtained. Units of the same type may be arranged in parallel or units of different types may be arranged. Next, the types of the arrangement and integration will be described by reference to respective figures. However, it is to be understood that the present invention is not construed as being restricted thereto and thus various combinations may be also employed depending on the purpose.

Figure 16:
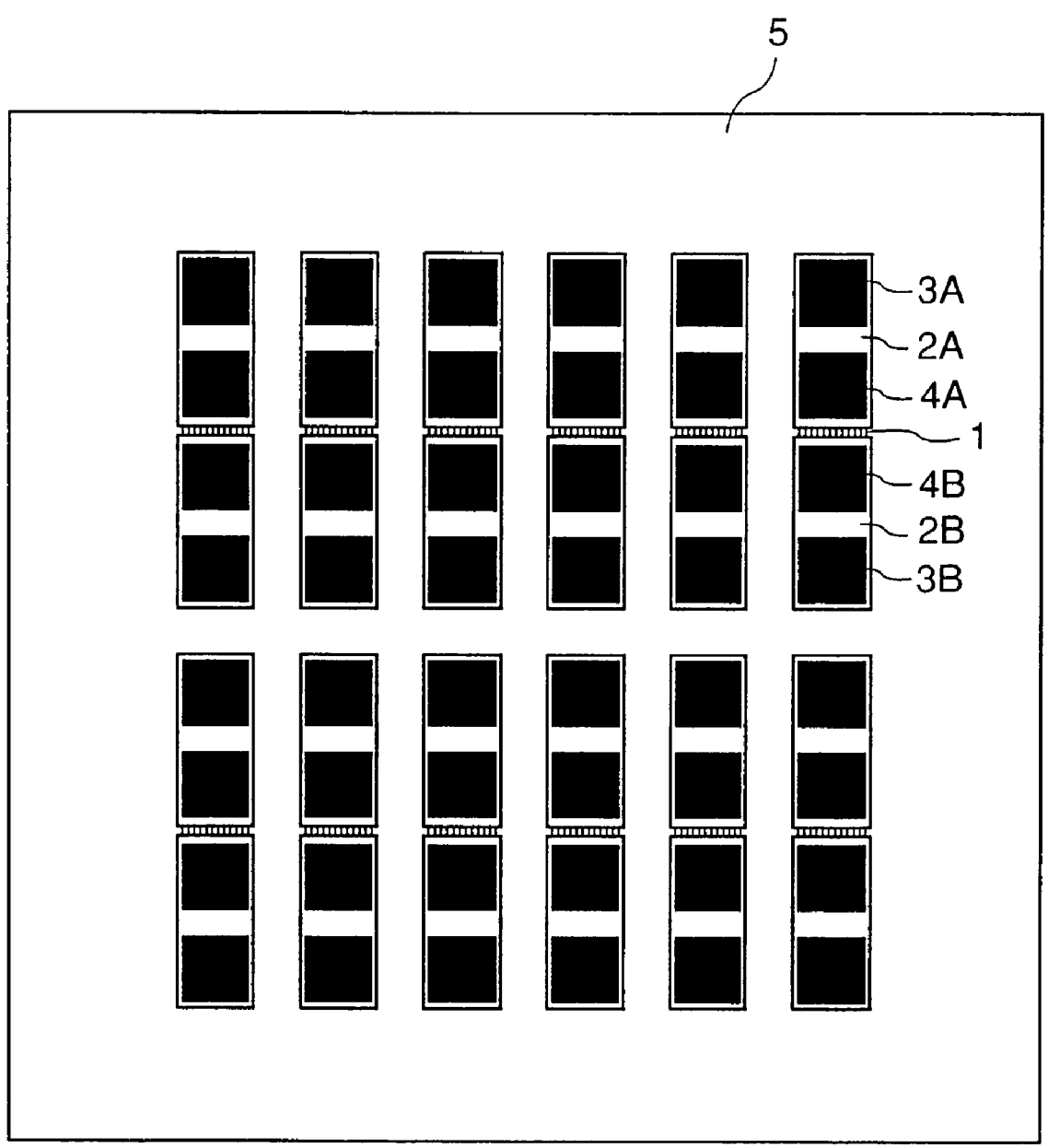
FIG. 16 shows an example of an integration of multiplicity of units wherein the units are all in the same type.

FIG. 16 shows an example wherein 12 well units each having a couple of wells connected via a channel as shown in FIG. 4 are mounted on a square substrate 7 (16 mm×16 mm). In this example, the units are each 5.7 mm in the major sides and 1.2 mm in the minor sides and located at intervals of 0.8 mm.

Figure 17:
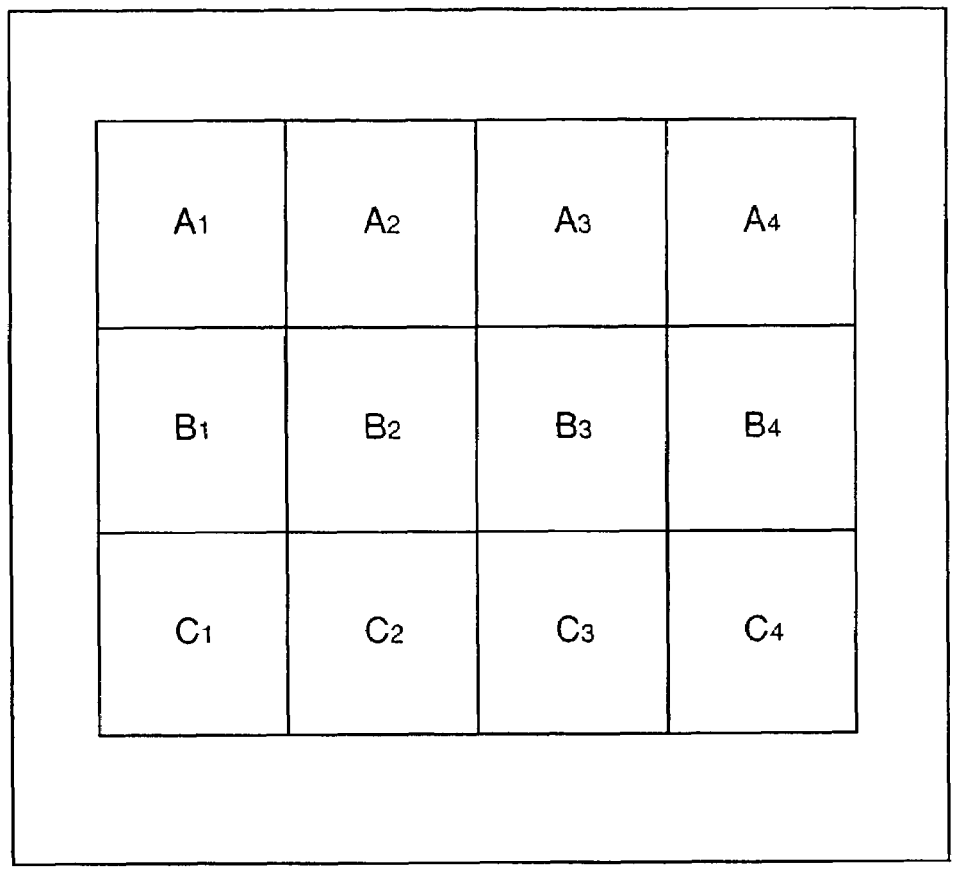
FIG. 17 shows an example of an integration of multiplicity of units wherein the units are in different types.

FIG. 17 shows an example of an integration of multiplicity of integrated units. In FIG. 17, each of quadrilaterals $A_{1-4}$, $B_{1-4}$ and $C_{1-4}$ corresponds to the integration shown by FIG. 16. In this case, the arrays A, B and C are integrations of units of different types.

Figure 18:
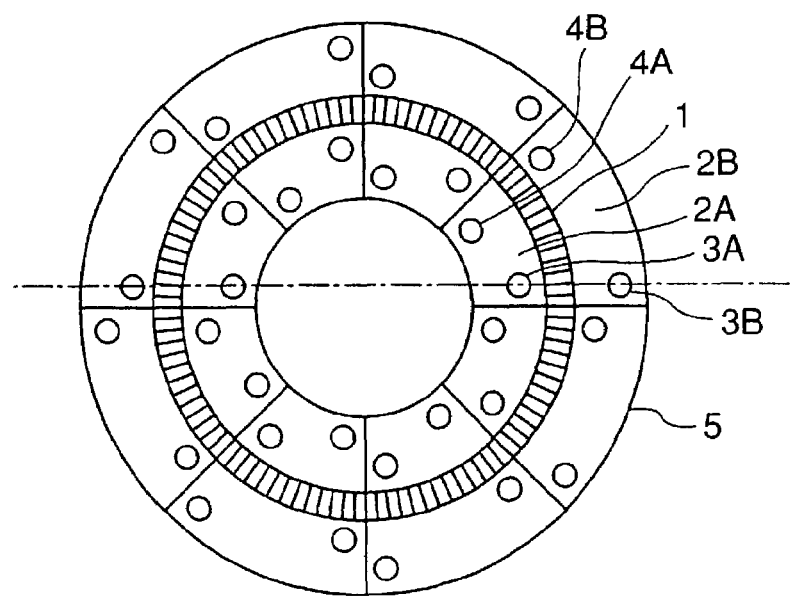
FIG. 18 shows an example wherein multiplicity of units are circularly integrated.
Figure 19:
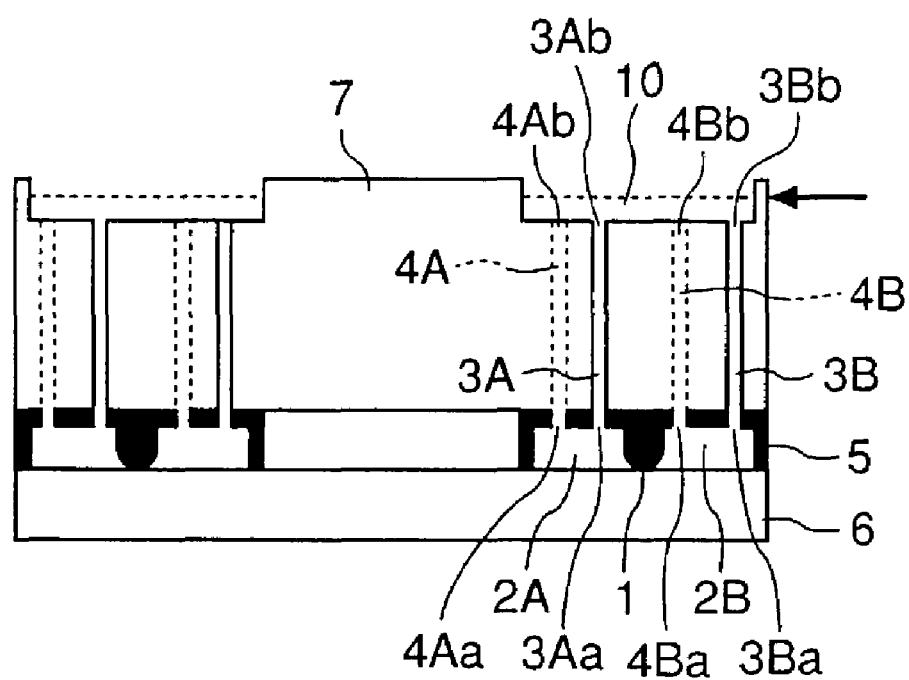
FIG. 19 is a sectional view along the dashed dotted line in FIG. 18.

FIG. 18 shows an example wherein independent double system units are integrated circularly. FIG. 19 is a sectional view of the unit of FIG. 18 along the dashed and dotted line. Concerning the size, for example, the width of wells 2A and 2B in the radial direction is 1.5 mm, the width of a channel 1 in the redial direction is 0.5 mm and the width of grooves13 formed in the channel 1 is 10 μm. In this case, the radius of the whole unit is 5.0 mm.

Figure 26:
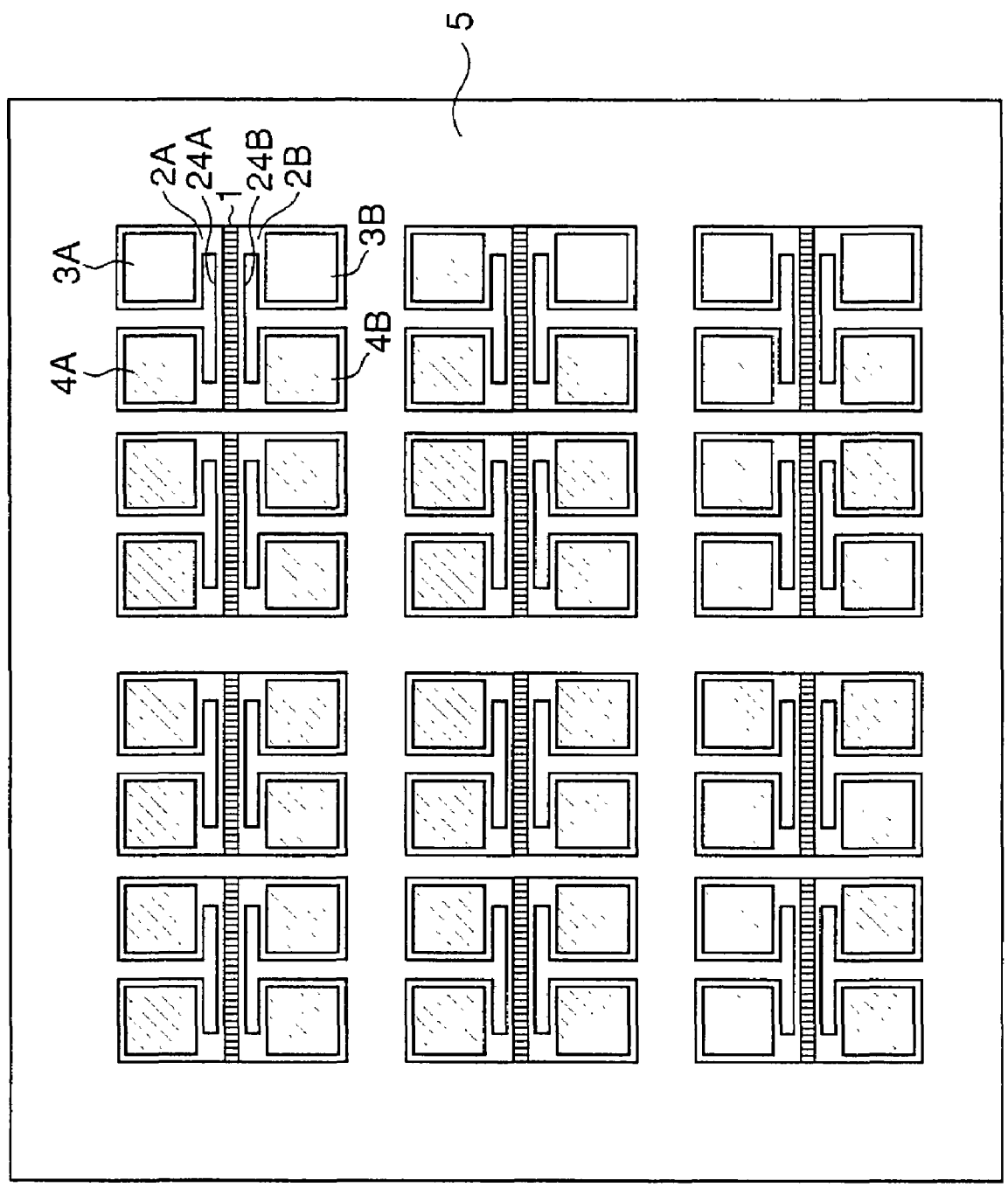
FIG. 26 shows an arrangement example wherein the wells shown by FIG. 24 are integrated.

FIG. 26 shows an example wherein 12 units of the type shown by FIG. 24 are integrated.

Figure 20:
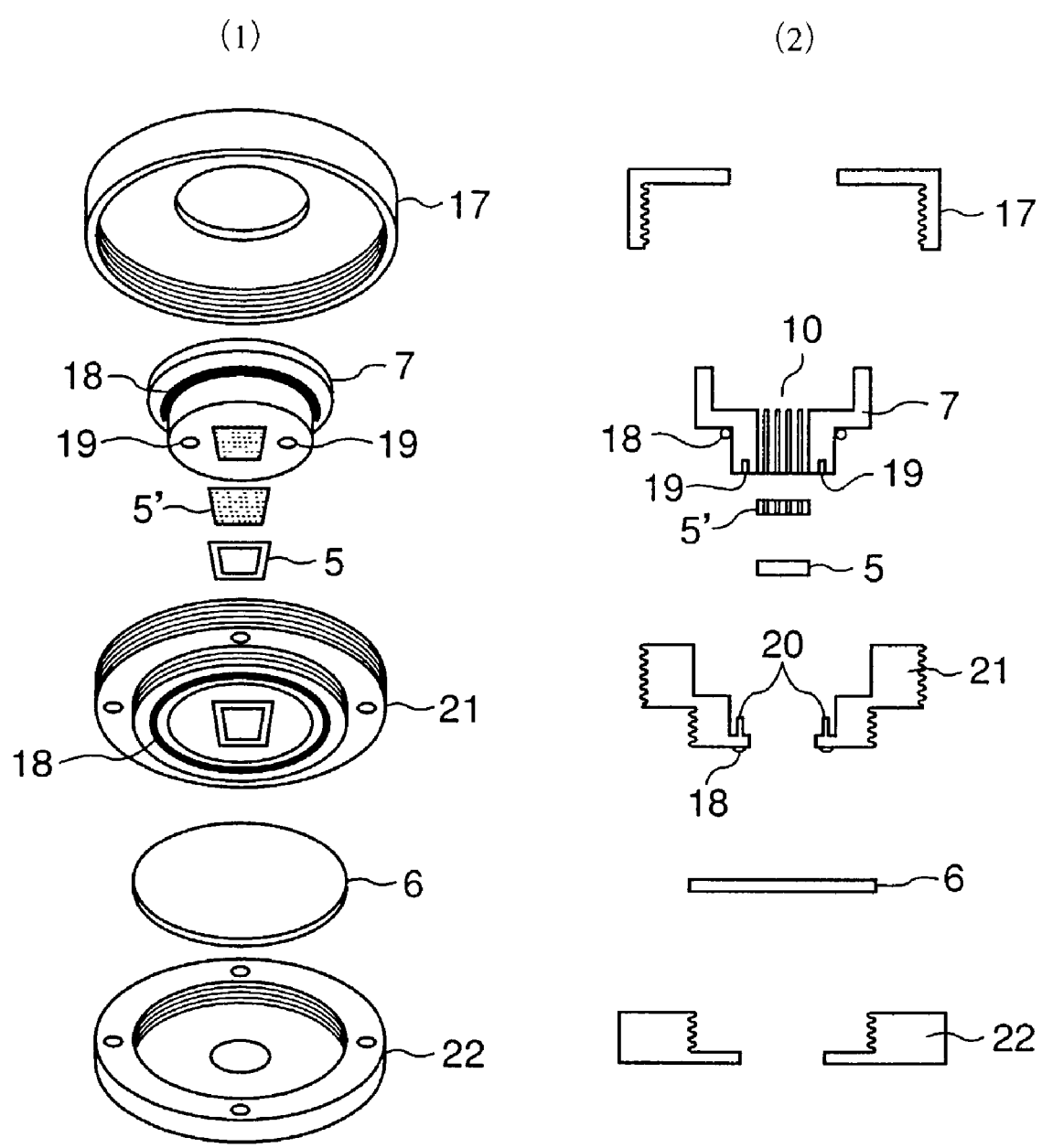
FIG. 20 shows an example of the fabrication of an apparatus for detecting chemotaxis of cells or separating chemotactic cells wherein (1) is perspective views of individual parts and (2) is sectional views corresponding thereto.

In such a case of integrating multiplicity of units, a single block 7 and a single glass substrate 6 may be used so as to cover the whole unit (see FIG. 20).

FIG. 20 shows an example of the fabrication of an apparatus for detecting chemotaxis of cells and separating chemotactic cells comprising multiplicity of units integrated together. A substrate 5 having multiplicity of units integrated thereon, a packing 5' and a block 7 covering them are placed between a cover cap 17 and an intermediate base 21. A glass substrate 6 is placed between the intermediate base 21 and a bottom base 22 and fastened with screws. The locations of the block 7 and the substrate 5 are specified by the intermediate base 21 and fixed by guide pins 20 and guide pin receiver holes 19 provided at the bottom face of the block 7. Alternatively, the substrate 5 may be directly pressed and fixed to the block 7.

In FIG. 20, it is also possible that a substrate 5 having a single unit (i.e., a couple of wells and a channel) is used as a substitute for the integrated unit and a plural number of the fabricated units are arranged at definite intervals. In this case, units can be successively exchanged.

8) Automatic Controlling System

Next, the automatic controlling system in the micro-sample treatment apparatus according to the present invention will be illustrated in detail by reference to an apparatus for detecting chemotaxis of cells as an example. However, it is needless to say that this illustration is given merely by way of example and various embodiments may be further employed for achieving the automation.

Figure 27:
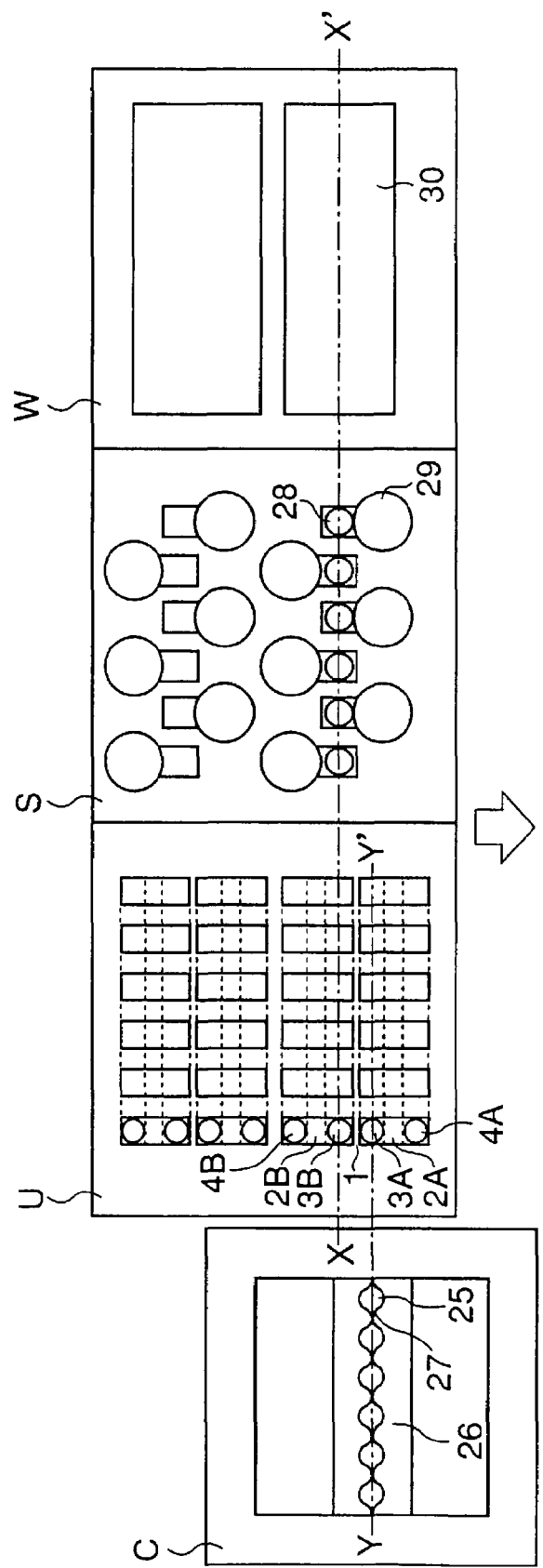
FIG. 27 shows an example of an automatic controlling system of the apparatus according to the present invention.

FIG. 27 shows an example of the automatic controlling system of the apparatus for detecting chemotaxis of cells according to the present invention. In FIG. 27, U represents a unit part, C represents a cell reservoir, S represents a specimen reservoir and W represents a pipette washing part. The line X-X' shows an example of the flow line of a plural number of specimen supply pipettes (6 in this case) aligned laterally, while the line Y-Y' shows an example of the flow line of a plural number of cell supply pipettes aligned laterally. The unit part U is set at the pipette flow line position and a space provided above the top ends of each unit is filled up with a liquid. Cells are held in the cell reservoir, while various specimens are held in the specimen reservoir S. Liquid level control pipettes aligned laterally are located above the unit part 4B to 4A and the flow line thereof is indicated by, for example, Z-Z' in FIG. 28. Each pipette is moved, for example, as follows, though it is needless to say that the present invention is not restricted thereto.

A definite amount of a cell suspension is sucked from the cell reservoir C by a cell supply pipette. Then the pipette moves along the flow line Y-Y' to the unit part U and supplies the cell suspension into the well 2A of each unit through a cell supply tube 3A. Subsequently, the cell supply pipette returns to the position C and stops the operation, or moves to supply the cell suspension to the next unit. Since cells are precipitated owing to the gravity, it is favorable to stir the cell suspension contained in the cell-reserving container 25 immediately before collecting the cells by sucking.

Figure 28:
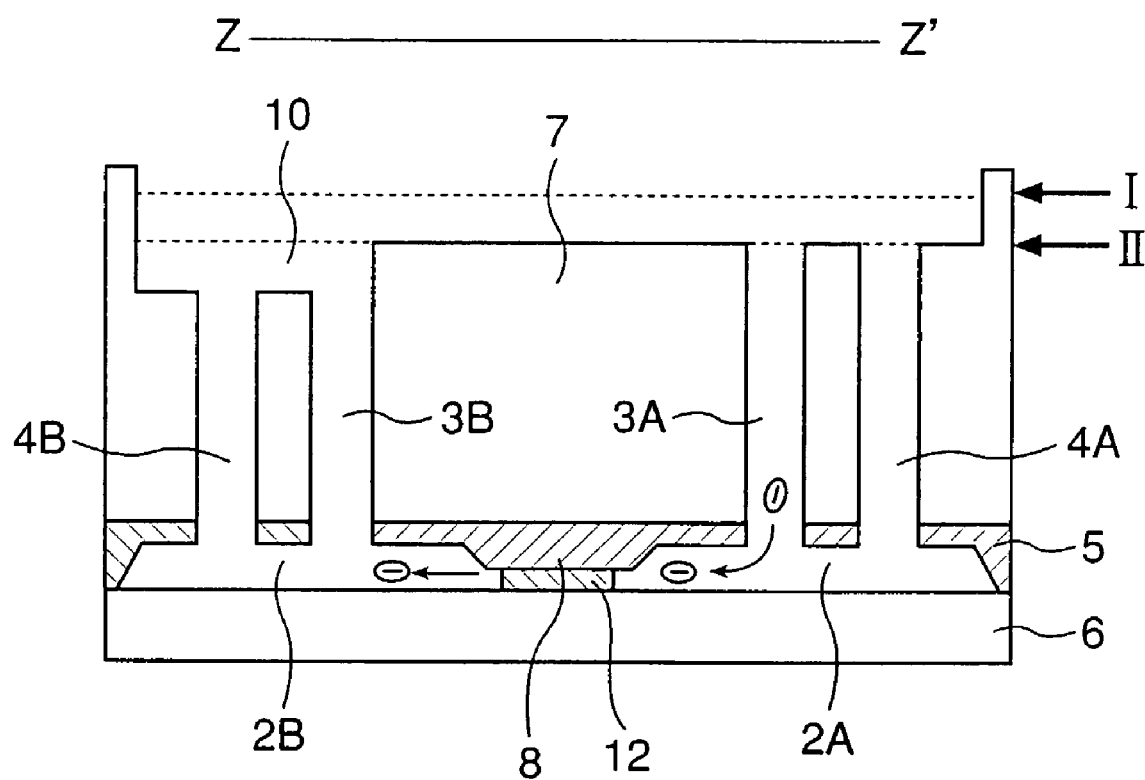
FIG. 28 shows the movement of liquid level control pipette(s).

Next, the liquid in the space 10 in each unit is sucked by a liquid level control pipette and thus the liquid level is lowered to the position II, as FIG. 28 shows. Subsequently, a definite amount of the liquid is further sucked so as to adjust the position of cells in the well 2A. Then the liquid level control pipette is elevated to the liquid level I position or higher and the sucked liquid is discharged at any point on the flow line Z-Z, thereby returning the liquid level in the space 10 to the position I. Subsequently, the liquid level control pipette is further elevated and stops its operation, or moves on the next unit.

Then a definite amount of a specimen is sucked from the specimen reservoir S by a specimen supply pipette. The specimen supply pipette moves along the flow line X-X' to the unit part U and supplies the specimen into the well 2B through a specimen supply tube 3B. Subsequently, the specimen supply pipette moves along the flow line X-X' to the pipette washing part W wherein it is washed by repeatedly sucking and discharging a washing liquor in a washing tank. Then the pipette is elevated above the liquid level in the washing tank and stops its operation, or moves to the next unit part U to supply the specimen.

Next, the unit part U having the cell suspension and the specimen thus supplied moves in the direction indicated by an arrow→in FIG. 27 and stops at the position where the channel 1 agrees with the detection part. Thus, the conditions of the cells are detected and recorded. As the unit part U moves, the next unit part U comes to the position of the pipette flow line and thus the above operations are repeated. It is also possible to move the unit part U together with the specimen reservoir S. In this case, the unit part U and the specimen reservoir S moves together and thus the next unit part U and the next specimen reservoir S come to the pipette flow line.

Figure 29:
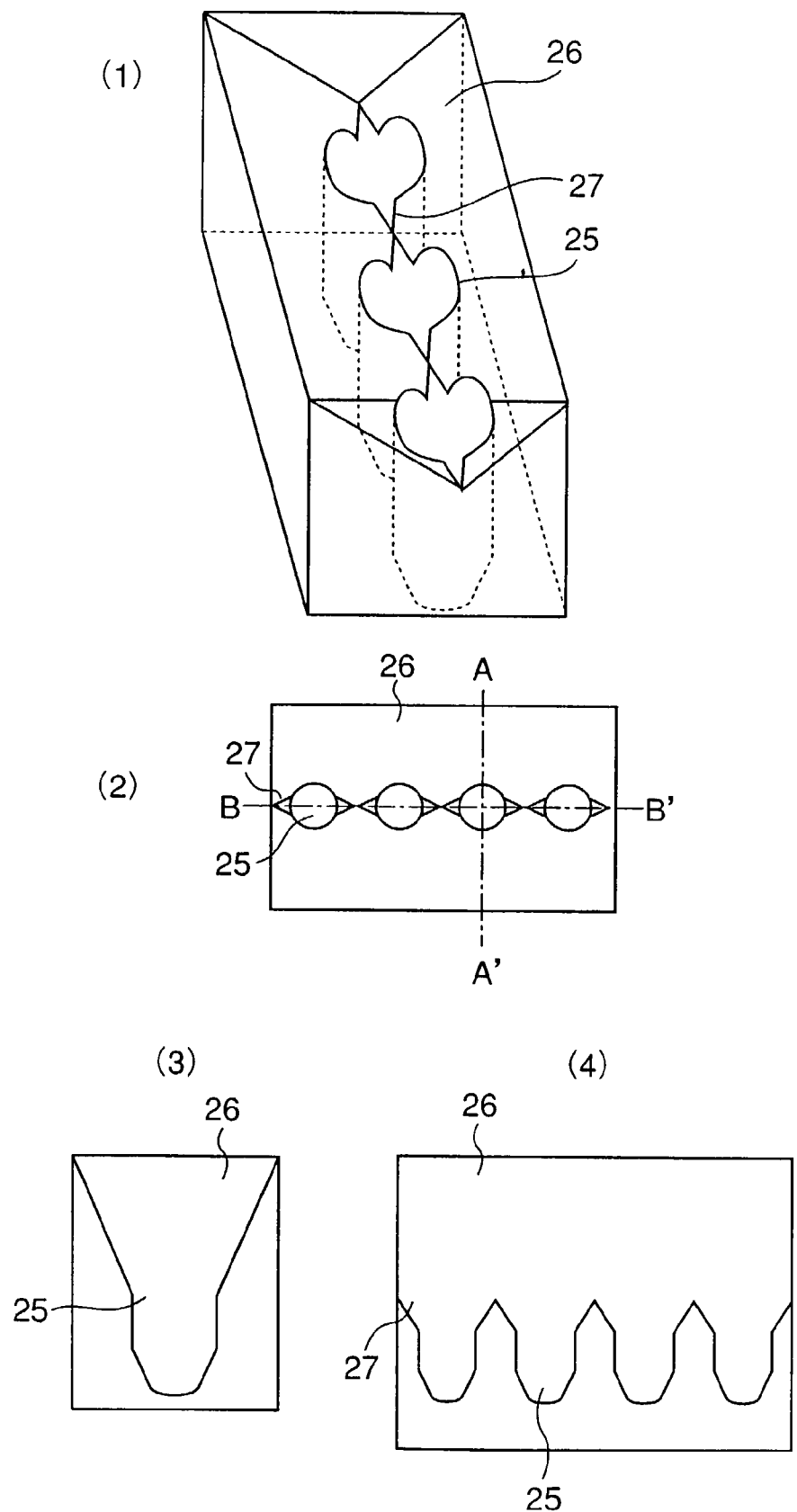
FIG. 29 shows an example of containers in a cell reservoir.

The cell reservoir C is provided with containers for temporarily holding cells to be supplied into the unit part U. These containers may be in any shape, so long as they can play the desired role. FIG. 29 shows an example of the containers in the cell reservoir C. A plural number of cell containers 25 are provide,d corresponding to the arrangement of each unit and a plural number of the cell supply pipettes. In the example shown by FIG. 29, an inclined injection part 26 is formed to facilitate the injection of cells into each container and avoid waste of cells. It is preferable to further provide an inlet part 27 so that the cell suspension can be easily introduced into the containers without waste. By using this structure, the cell suspension injected at an arbitrary point can be supplied into all containers, thereby saving a lot of time and labor for injecting the cell suspension into individual cells. It is also preferable that the cell containers 25 are tapered at the bottom so as to avoid waste of the cell suspension in the step of sucking by the pipettes. In FIG. 29, (1) is a perspective view; (2) is a top plan view; (3) is a sectional view along the dotted line A-A' in (2); and (4) is another sectional view along the dotted line B-B' in (2).

Figure 30:
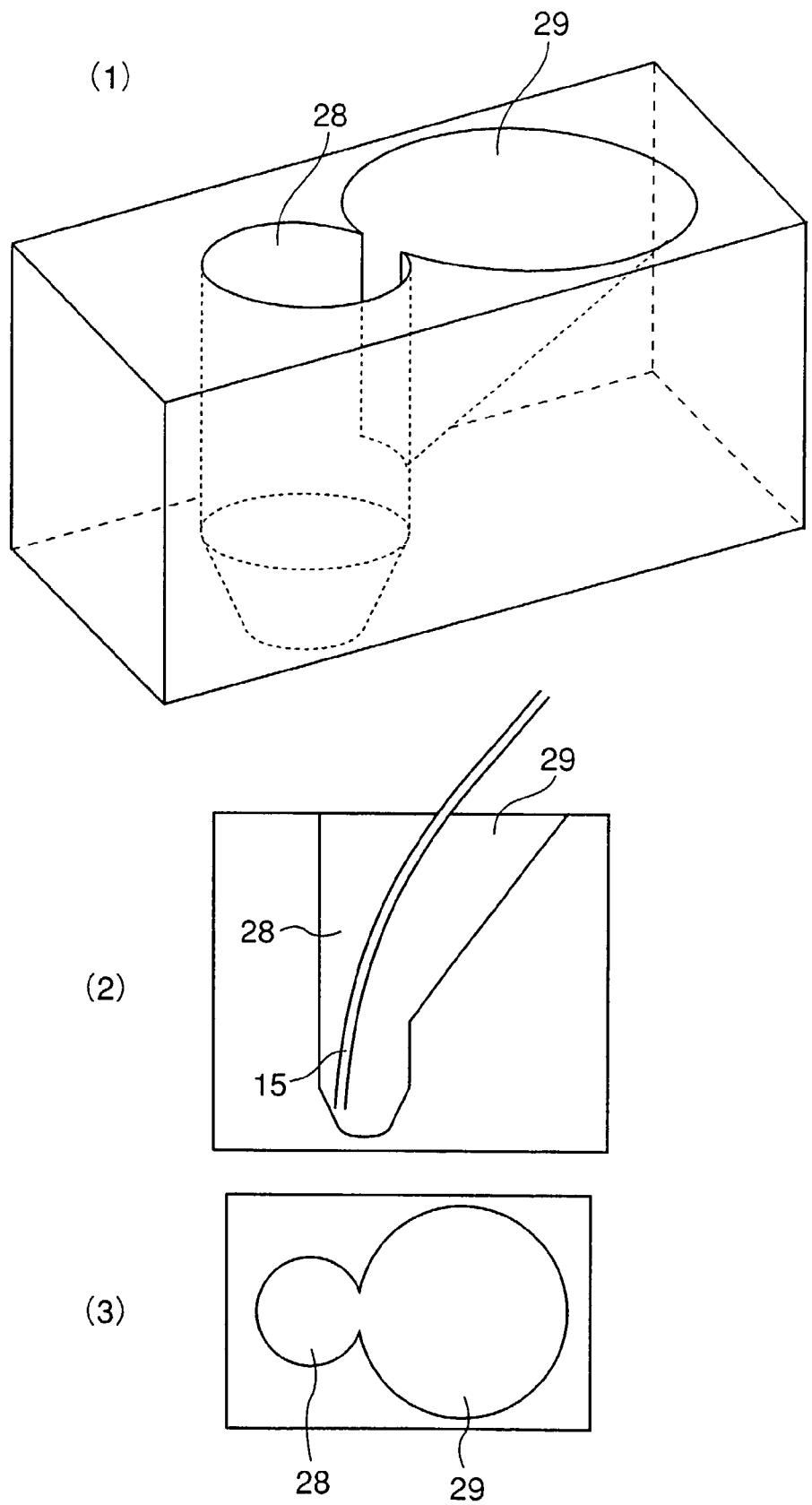
FIG. 30 shows an example of a container in a specimen reservoir.
Figure 31:
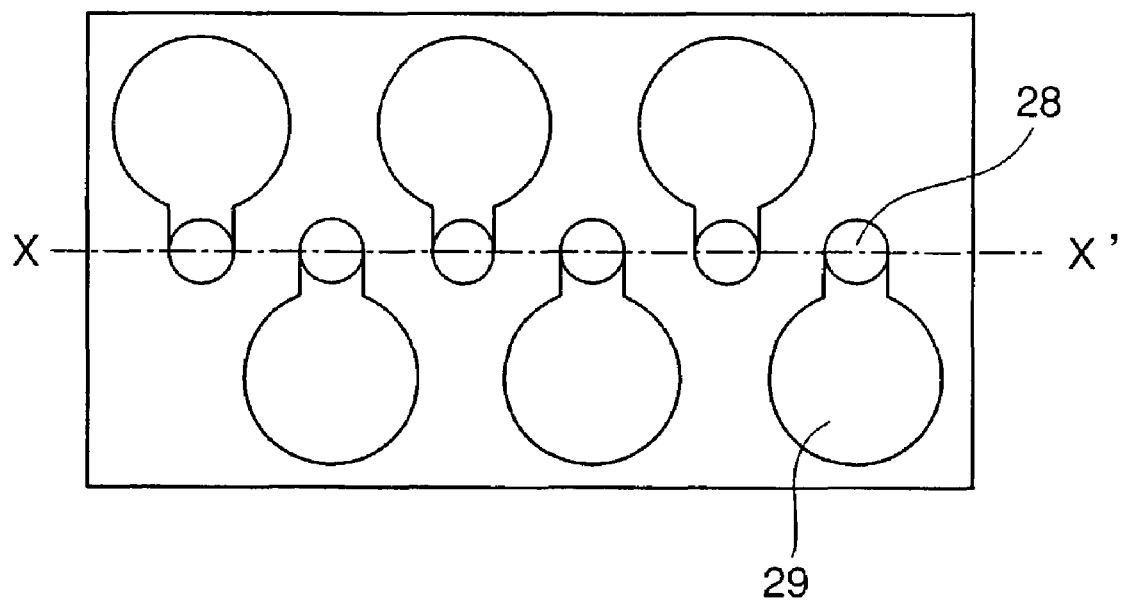
FIG. 31 shows an arrangement example of the containers shown by FIG. 30 in the specimen reservoir.
Figure 32:
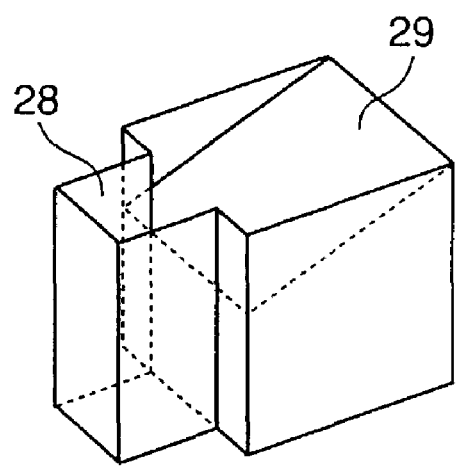
FIG. 32 shows another example of a container in the specimen reservoir.
Figure 33:
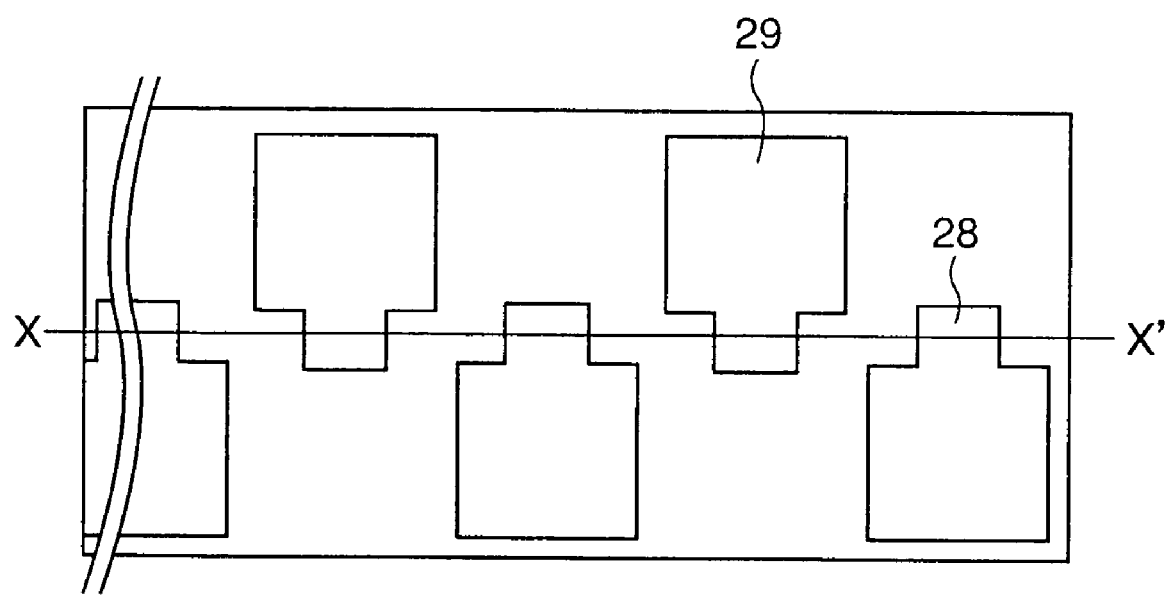
FIG. 33 shows an arrangement example of the containers shown by FIG. 32 in the specimen reservoir.

The specimen reservoir S is provided with containers for temporarily holding a specimen to be supplied into the unit part U. These containers may be in any shape, so long as they can play the desired role. In case of supplying many types of specimens into the unit part U, use is frequently made of a method wherein individual specimens are manually injected into the containers in the specimen reservoir S with the use of micropipettes, etc. In such a case, it is preferable to provide pipette tip inlet ports 29 having a diameter larger than the pore size of the opening of the containers, as shown in FIG. 30. It is also desirable that the containers are tapered at the bottom to lessen the specimen remaining therein after taking out from the containers, as shown by FIG. 30. In FIG. 30, (1) is a perspective view; (2) is a sectional view; and (3) is a top plan view. In the example shown by FIG. 30(2), the pipette tip 34 is inserted into the container 28 from the pipette tip inlet port 29 in the step of manually injecting a specimen. FIG. 31 shows an example wherein a plural number of specimen containers are located along the flow line X-X' of the specimen supply pipette. As FIG. 31 shows, the inlet ports may be alternately located so that the intervals among the containers can be adjusted fit to the intervals among the units in the unit part U. The specimen containers may have a square shape, as shown by FIG. 32. FIG. 33 shows an example wherein a plural number of specimen containers are located along the flow line X-X' of the specimen supply pipettes.

Figure 34:
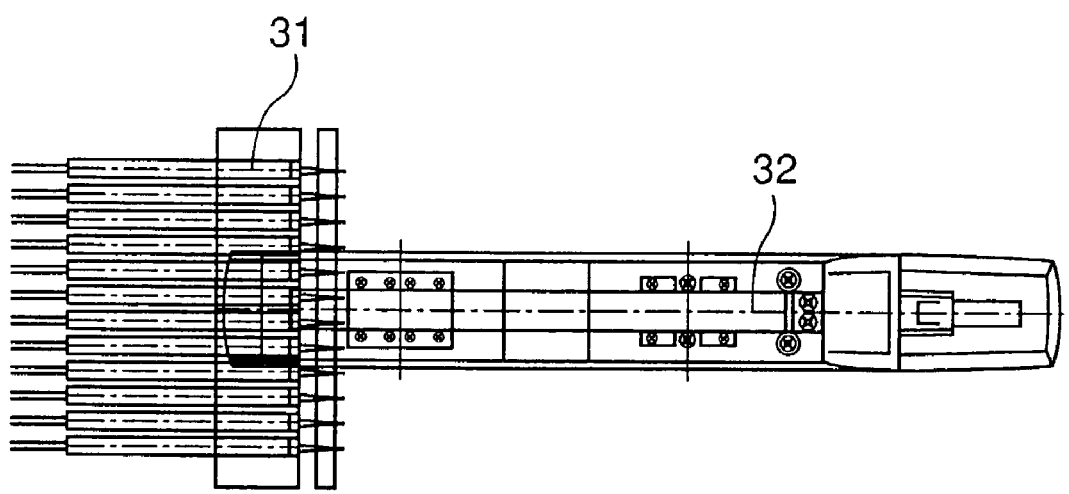
FIG. 34 shows an example of a pipette to be used in the present invention.
Figure 34:
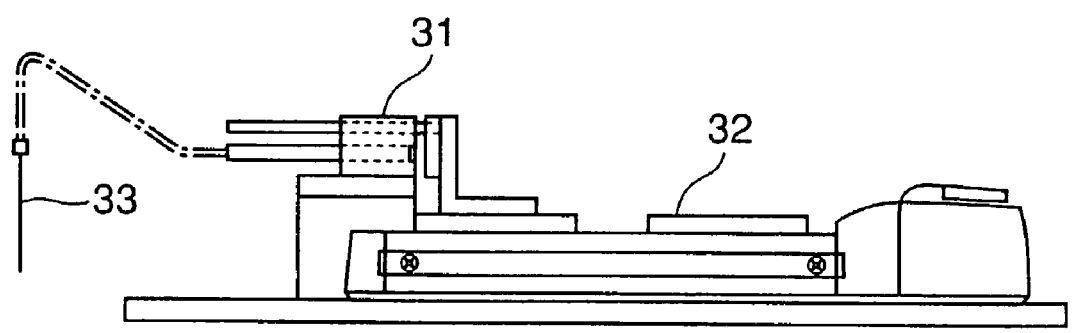

In the pipettes to be used in the apparatus according to the present invention, suction and discharge of liquids can be controlled by computerized programming. It is preferable to use a pipette having a multichannel syringe as shown by FIG. 34. The needle (tip) of the pipette may be made of glass, a metal, a plastic material, etc. In FIG. 34, (1) is a top plan view; and (2) is a side plan view.

The detection means to be used in the present invention may be any means so long as cells which are passing through a channel or have passed therethrough can be detected thereby. If necessary, it involves a means of recording the detection data. Any means known as a means of detecting and recording cells is usable therefor. Use can be made of, for example, a microscope optionally combined with a video camera. It is also possible to employ a system having an objective lens provided with a CCD camera. For the detection in integrated units, it is preferable to employ a system wherein the channels of the units are successively scanned along with an objective lens.

As shown by FIG. 4, the detection means is usually provided in a channel of a unit. In an apparatus having multiplicity of units integrated together, it is also possible to employ a system wherein arrays of the units successively come to a detection part located at a definite position for detection and recording. In this case, the channels of the aligned units are scanned with the detector. Either one or more scanning detectors may be employed. Owing to this constitution, a relatively small number of detectors suffice for the detection in multiplicity of integrated units.

Cells which are passing or have passed through a channel can be detected and counted by directly observing the cells with a microscope. Alternatively, the detection and counting can be easily performed by preliminarily labeling the cells with a luminous or fluorescent substance and then capturing the luminescence or fluorescence in a conventional manner.

INDUSTRIAL APPLICABILITY

According to the structure of the present invention, it is possible to, in the step of injecting a liquid sample into a well, prevent the migration of the sample into another well or overflow thereof. Moreover, the position of the injected sample can be adjusted in a well or the sample can be transferred into the next well under controlling.

The structure according to the present invention achieves a remarkable technical merit and widely applicable particularly in cases of handling samples in microquantities such as solutions and cell suspensions, or separating cells or particles depending on size.

A high technical merit can be established by applying the structure of the present invention to an apparatus for detecting chemotaxis of cells or an apparatus for separating cells with the use of cell chemotaxis. That is to say, unexpected migration of a sample caused by pressure changes in the step of injecting/sucking samples such as cells and specimen solutions can be prevented thereby. Furthermore, unexpected migration of a sample caused by horizontal off balance of the apparatus can be prevented. Thus, movements of cells by their own actions can be accurately understood or desired cells can be taken out. Namely, it is possible to obtain results affected by both of the effect of a chemotactic factor or an inhibitor and the characteristics of the cells.

In the apparatus for detecting chemotaxis of cells or the apparatus for separating cells with the use of cell chemotaxis according to the present invention, a bank is formed in a channel located between wells or barriers constituting definite grooves are formed on the bank or, alternatively, a gap is formed between a plane provided on the upper face of the bank and a glass substrate. Owing to this structure, it becomes possible to easily establish the state wherein cells are brought together in the vicinity of the channel and aligned in the flow direction of the cells, when a cell suspension is put into one well and an adequate amount of a liquid is sucked from the other well. As a result, the presence/absence of the cell chemotaxis can be accurately detected.

The structure according to the present invention makes it possible to downsize the apparatus. When applied to an apparatus for detecting chemotaxis of cells or separating chemotactic cells, namely, samples can be used in an amount 1/50 to 1/1000 times as much in the conventional cases with the use of a Boyden chamber. That is to say, biological samples (whole blood, etc.) per se are usable as samples in the apparatus of the present invention. By using whole blood as a sample, for example, measurement can be made by using 0.1 µl of blood in case of detecting the chemotaxis of neutrophils and about 1 µl of blood in case eosinophils, monocytes or basophils.

In the structure according to the present invention, moreover, no delicate control is needed in the step of injecting a liquid, which brings about an additional merit that the apparatus can be easily automated.

The unit of the apparatus according to the present invention can be in a microsize and thus multiplicity of the units can be integrated together, which brings about another merit that an apparatus whereby a large number of samples can be simultaneously treated can be fabricated. In this case, an apparatus having an automated system of injecting and detecting liquids can be easily fabricated.

In integrating multiplicity of units, detection and separation for different purposes can be simultaneously carried out by combining and integrating units of different types together. Thus, the treatment efficiency can be elevated. In case of an apparatus for detecting chemotaxis of cells, for example, the detection of various chemotactic factors or inhibitors for a single type of cells or the detection of the chemotaxis of different types of cells for a single chemotactic factor can be carried out at once.

The invention claimed is:

1. A microsample treatment apparatus, which comprises:
   a) a plurality of wells;
   b) said plurality of wells brine connected to each other via a part having resistance to fluids, said part being selected from the group consisting of one or more thin pipes, narrow gaps, narrow cap having barriers, thin grooves, filters, resin-filled columns and other structures through which a fluid can be passed but which have resistance to fluids; and
   c) each of the wells being provided with at least one tube for injecting/sucking a sample, wherein
   1) said apparatus has a space in common at the top ends of said tubes in which a liquid is held to maintain said liquid in said wells and said part having resistance to fluids under a definite pressure,
   2) the level of said liquid can be controlled to adjust the position of said sample in said well(s) or transfer said sample into the other well(s) across the part having resistance, to fluids, and
   3) the top end of at least one tube formed in a well is located higher than top ends of the tubes formed in one or more wells across the part having resistance to fluids.

2. The microsample treatment apparatus as claimed in claim 1, wherein each of the wells has a single tube.

3. The microsample treatment apparatus as claimed in claim 1, wherein each of the wells has a plurality of said tubes.

4. A microsample treatment apparatus which comprises:
   a) an integration unit having a plural number of units of the same or different types on a single substrate or a plural number of integration units on a single substrate;
   b) said unit which has a plural number of wells;
   c) said plurality of wells being connected to each other via a part having resistance to fluids, said part being selected from the group consisting of one or more thin pipes, narrow gaps, narrow gap having barriers, thin grooves, filters, resin-filled columns and other structures through which a fluid can be passed but which have resistance to fluids; and
   d) each of the wells being provided with at least one tube for injection/sucking a sample, wherein
   1) said unit has a space in common at the top ends of said tubes in which a liquid is held to maintain said liquid in said wells and said part having resistance to fluids under a definite pressure and
   2) the level of said liquid can be controlled to adjust the position of said sample in said well(s) or transfer said sample into the other well(s) across the part having resistance to fluids, and
   3) the top end of at least one tube is formed in a, well located higher than top ends of the tubes formed in one or more wells across the , part having resistance to fluids.

5. The microsample treatment apparatus as claimed in claim 4, wherein each of the wells has a single tube.

6. The microsample treatment apparatus as claimed in claim 4, wherein each of the wells has a plurality of said tubes.

7. An apparatus for detecting chemotaxis of cells or separating chemotactic cells, which comprises:
   a) a plurality of wells;
   b) said plurality of wells being connected to each other via a channel having a width fit for a diameter or deformability of cells; and
   c) each of the wells being provided with at least one tube for injection/sucking a sample, wherein
   1) said apparatus has a space in common at the top ends of said tubes in which a liquid is held to maintain said liquid in said wells and said channel under a definite pressure,
   2) the level of said liquid can be controlled to adjust the position of the cells in said well(s), and
   3) the top end of at least one tube formed in well for holding cells is located higher than top of the formed in one or more wells across the channel.

8. The apparatus for detecting chemotaxis of cells or separating, chemotactic cells as claimed in claim 7, wherein each of the wells has a single tube.

9. The apparatus for detecting chemotaxis of cells or separating chemotactic cells as claimed in claim 7, wherein each of the wells has a plurality of said tubes.

10. An apparatus for detecting chemotaxis of cells or separating chemotactic cells which comprises:
    a) an integration unit having a plural number of units of the same or different types on a single substrate or a plural number of integration units on a single substrate;
    b) said each unit has a plural number of wells;
    c) said plural number of wells being connected to each other via a channel having a width fit for a diameter or deformability of cells; and
    d) each of the wells being provided with at least one tube for injection/sucking a sample, wherein
    1) said unit has a space in common at the top ends of said tubes in which a liquid is held to maintain said liquid in said wells and said channel under a definite pressure,
    2) the level of said liquid can be controlled to adjust the position of the cells in said well(s), and
    3) the top end of at least one tube formed in a well for holding cells is located higher than top ends of the tubes formed in one or more wells across the channel.

11. The apparatus for detecting chemotaxis of cells or separating chemotactic cells as claimed in claim 10, wherein each of the wells has a single tube.

12. The apparatus for detecting chemotaxis of cells or separating chemotactic cells as claimed in claim 10, wherein each of the wells has a plurality of said tubes.

* * * * *